United States Patent
Bridger et al.

(10) Patent No.: US 7,169,750 B2
(45) Date of Patent: Jan. 30, 2007

(54) METHODS TO MOBILIZE PROGENITOR/STEM CELLS

(75) Inventors: Gary Bridger, Bellingham, WA (US); Michael J. Abrams, Custer, WA (US); Geoffrey W. Henson, Ferndale, WA (US); Ronald T. MacFarland, Vancouver (CA); Gary B. Calandra, Cresco, PA (US)

(73) Assignee: Anormed, Inc., Langley (CA)

( * ) Notice: Subject to any disclaimer, the term of this patent is extended or adjusted under 35 U.S.C. 154(b) by 461 days.

(21) Appl. No.: 10/456,942

(22) Filed: Jun. 5, 2003

(65) Prior Publication Data
US 2005/0043367 A1 Feb. 24, 2005

Related U.S. Application Data

(63) Continuation-in-part of application No. 10/209,001, filed on Jul. 30, 2002, now Pat. No. 6,987,102.

(60) Provisional application No. 60/382,155, filed on May 20, 2002, provisional application No. 60/309,196, filed on Jul. 31, 2001.

(51) Int. Cl.
A61K 38/00 (2006.01)
A61K 31/44 (2006.01)
A61K 31/40 (2006.01)

(52) U.S. Cl. .......................... 514/2; 514/357; 514/408; 514/649

(58) Field of Classification Search ...................... None
See application file for complete search history.

(56) References Cited

U.S. PATENT DOCUMENTS

| 5,021,409 A | 6/1991 | Murrer et al. ............... 514/183 |
| 5,582,823 A | 12/1996 | Souza ....................... 424/85.2 |
| 5,583,131 A | 12/1996 | Bridger et al. .............. 514/183 |
| 5,606,053 A | 2/1997 | Prashad et al. ............. 540/474 |
| 5,612,478 A | 3/1997 | Xu et al. .................... 540/474 |
| 5,698,546 A | 12/1997 | Bridger et al. .............. 514/183 |
| 5,756,728 A | 5/1998 | Xu et al. .................... 540/474 |
| 5,801,281 A | 9/1998 | Xu et al. ...................... 564/82 |
| 5,817,807 A | 10/1998 | Bridger et al. ............. 540/474 |
| 6,001,826 A | 12/1999 | Murrer et al. .............. 514/183 |
| 6,365,583 B1 | 4/2002 | MacFarland et al. |
| 6,667,320 B2 | 12/2003 | Bridger et al. |
| 6,670,354 B2 | 12/2003 | MacFarland et al. |
| 6,987,102 B2 | 1/2006 | Bridger et al. |
| 2002/0058653 A1 | 5/2002 | MacFarland et al. |
| 2002/0156034 A1 | 10/2002 | Tudan et al. |
| 2004/0102428 A1 | 5/2004 | Bridger et al. |

FOREIGN PATENT DOCUMENTS

| WO | WO 00/02870 | 1/2000 |
| WO | WO-00/45814 | 8/2000 |
| WO | WO 00/56729 | 9/2000 |
| WO | WO 01/44229 | 6/2001 |
| WO | WO 01/85196 | 11/2001 |
| WO | WO 02/22599 | 3/2002 |
| WO | WO 02/22600 | 3/2002 |
| WO | WO 02/26721 | 4/2002 |
| WO | WO 02/34745 | 5/2002 |
| WO | WO 02/58653 | 8/2002 |

OTHER PUBLICATIONS

AM Smits, et al., J. Cell. Mol. Med. (2005) vol. 9(1), pp. 25-36.*
Aiuti et al. "The Chemokine SDF-1 is a Chemoattractant for Human CD34+ Hematopoietic Progenitor Cells and Provides a New Mechanism to Explain the Mobilization of CD34+ Progenitors to Peripheral Blood" J. Exp. Med. 185:111-120 (1997).
Bleul et al. "A Highly Efficacious Lymphocyte Chemoattractant Stromal Cell-Derived Factor 1 (SDF-1)" J. Exp. Med. 184:1101-1109 (1996).
Broxmeyer et al. "Effects of In Vivo Treatment with PIXY321 (GM-CSF/IL-3 Fusion Protein) on Proliferation Kinetics of Bone Marrow and Blood Myeloid Progenitor Cells in Patients with Sarcoma" Exp. Hematol. 23:335-340 (1995).
Broxmeyer et al. "Myeloid Progenitor Cell Proliferation and Mobilization Effects of BB10010, a Genetically Engineered Variant of Human Macrophage Inflammatory Protein-1α, in a Phase I Clinical Trial in Patients with Relapsed/Refractory Breast Cancer" Blood Cells, Molecules and Diseases 24:14-30 (1998).

(Continued)

*Primary Examiner*—B. Dell Chism
(74) *Attorney, Agent, or Firm*—Morrison & Foerster LLP

(57) ABSTRACT

Methods to elevate progenitor and stem cell counts in animal subjects using compounds which bind to the chemokine receptor CXCR4 are disclosed. Preferred embodiments of such compounds are of the formula Z-linker-Z'   (1)

or pharmaceutically acceptable salt thereof
wherein Z is of the formula

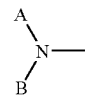

wherein A comprises a monocyclic or bicyclic fused ring system containing at least one N and B is H or an organic moiety of 1–20 atoms,
Z' is of the formula —Ar(Y)$_j$;

wherein Ar is an aromatic or heteroaromatic moiety, and each Y is independently a non-interfering substituent and j is 0–3; and
"linker" represents a bond, alkylene (1–6C) or may comprise aryl, fused aryl, oxygen atoms contained in an alkylene chain, or may contain keto groups or nitrogen or sulfur atoms.

21 Claims, 1 Drawing Sheet

OTHER PUBLICATIONS

Croop et al. "Large Scale Mobilization and Isolation of CD34+ Cells from Normal Donors" Bone Marrow Transplantation 26:1271-1279 (2000).

Dale et al. "Effects of Granulocyte-Macrophage Colony-Stimulating Factor(GM-CSF) on Neutrophil Kinetics and Function in Normal Human Volunteers" Am. J. of Hematol. 57:7-15 (1998).

Fedyk et al. "Maturation Decreases Responsiveness of Human Bone Marrow B Lineage Cells to Stromal-Derived Factor 1 (SDF-1)" J. Leukoc. Biol. 66:667-673 (1999).

Gear et al. "Adenosine Diphosphate Strongly Potentiates the Ability of the Chemokines MDC, TARC, and SDF-1 to Stimulate Platelet Function" Blood 97:937-945 (2001).

Glaspy et al. "Biology and Clinical Potential of Stem-Cell Factor" Cancer Chemother. Pharmacol. 38(Suppl.):S53-S57 (1996).

Glaspy et al. "Peripheral Blood Progenitor Cell Mobilization Using Stem Cell Factor in Conbimation with Filgrastim in Breast Cancer Patients" Blood 90:2939-2951 (1997).

Hodohara et al. "Stromal Cell-Derived Factor-1 (SDF-1) Acts Together with Thrombopoietin to Enhance the Development of Megakaryocytic Progenitor Cells (CFU-MK)" Blood 95:769-775 (2000).

Jackson et al. "Regeneration of Ischemic Cardiac Muscle and Vascular Endothelium by Adult Stem Cells" J. Clin. Invest 107:1395-1402 (2001).

Jo et al. "Chemotaxis of Primitive Hematopoietic Cells in Response to Stromal Cell-Derived Factor-1" J. Clin. Invest. 105:101-111 (2000).

King et al. "Rapid Mobilization of Murine Hematopoietic Stem Cells with Enhanced Engraftment Properties and Evaluation of Hematopoietic Progenitor Cell Mobilization in Rhesus Monkeys by a Single Injection of SB-251353, a Specific Truncated Form of the Human CXC Chemokine GROβ" Blood 97:1534-1542 (2001).

Kocher et al. "Neovascularization of Ischemic Myocardium by Human Bone-Marrow-Derived Angioblasts Prevents Cardiomyocyte Apoptosis, Reduces Remodeling and Improves Cardiac Function" Nature Med. 7:430-436 (2001).

Ma et al. "Impaired B-Lymphopoiesis, Myelopoiesis, and Derailed Cerebellar Neuron Migration in CXCR4- and SDF-1-Deficient Mice" Proc. Natl. Acad. Sci. USA 95:9448-9453 (1998).

Ma et al. "The Chemokine Receptor CXCR4 is Required for the Retention of B Lineage and Granulocytic Precursors within the Bone Marrow Microenvironment" Immunity 10:463-471 (1999).

Maekawa et al. "Chemokine/Receptor Dynamics in the Regulation of Hematopoiesis" Internal Med. 39:90-100 (2000).

Majka et al. "Stromal-Derived Factor 1 and Thrombopoitin Regulate Distinct Aspects of Human Megakaryopoiesis" Blood 96:4142-4151 (2000).

Nagasawa et al. "A Chemokine, SDF-1/PBSF, and Its Receptor, CXC Chemokine Receptor 4, as Mediators of Hematopoiesis" Int. J. Hematol. 72:408-411 (2000).

Peled et al. "Dependence of Human Stem Cell Engraftment and Repopulation of NOD/SCID Mice on CXCR4" Science 283:845-848 (1999).

Ponomaryov et al. "Induction of the Chemokine Stromal-Derived Factor-1 Following DNA Damage Improves Human Stem Cell Function" J. Clin. Invest. 106:1331-1339 (2000).

Pruijt et al. "Mechanisms Underlying Hematopoietic Stem Cell Mobilization Induced by the CXC Chemokine Interleukin-8" Cur. Op. In Hematol. 6:152-158 (1999).

Riviere et al. "Phenotypic and Functional Evidence for the Expression of CXCR4 Receptor During Megakaryocytopoiesis" Blood 95:1511-1523 (1999).

Rosenfeld et al. "Comparison of Four Cytokine Regimens for Mobilization of Peripheral Blood Stem Cells: IL-3 Alone and Combined with GM-CSF or G-CSF" Bone Marrow Transplantation 17:179-183 (1997).

Tachibana et al. "The Chemokine Receptor CXCR4 is Essential for Vascularization of the Gastrointestinal Tract" Nature 393:591-594 (1998).

Vadhan-Raj et al. "Stimulation of Megakaryocyte and Platelet Production by a Single Dose of Recombinant Human Thrombopoietin in Patients with Cancer" Ann. Intern. Med. 126:673-681 (1997).

Viardot et al. "The Human Immunodeficiency Virus (HIV)-Type 1 Coreceptor CXCR-4 (Fusin) is Preferentially Expressed on the More Immature CD 34+ Hematopoietic Stem Cells" Ann. Hematol. 77:194-197 (1998).

Voermana. "In Vitro Migratory Capacity of CD34+ Cells is Related to Hematopoietic Recovery After Autologous Stem Cell Transplantation" Blood 97:799-804 (2001).

Zou et al. "Function of the Chemokine Receptor CXCR4 in Haematopoiesis and in Cerebellar Development" Nature 393:595-599 (1998).

Moore et al., Ann. N.Y. Acad. Sci. (2001) 938:36-45.

Burdach, Klin. Padiatr. (1991) pp. 302-310.

CAS Registry No. 155148-31-5, accessed Apr. 1, 2005, 1 page.

ChemIDplus Lite Record, JM 3100, accessed Apr. 1, 2005, 1 page.

DiJulio, Oncol. Nurs. Forum. (1991) 18(2) Suppl.:3-6.

Finer, Washington Post (Mar. 31, 2005), p. A2.

Hendrix et al., Antimicrobial Agents and Chemotherapy (2000) 44(6):1667-1673.

NIAID Chemical Compound Search, 1,1'-[1,4-Phenylenebis(methylene)]bis[1,4,8,11-tetraazacyclotetradecane], accessed Apr. 1, 2005, 1 page.

Purves et al. (eds.), Life: The Science of Biology, Sinauer Associates, Inc. (1992) pp. 928-929.

Smits et al., J. Cell. Mol. Med. (2005) 9(1):25-36.

Szabo et al., British Journal of Pharmacology (1998) 125:379-387.

Witvrouw et al., Antiviral Chemistry and Chemotherapy (1996) 7(1):27-30.

\* cited by examiner

METHODS TO MOBILIZE PROGENITOR/STEM CELLS

CROSS-REFERENCE TO RELATED APPLICATIONS

This application is a continuation-in-part of U.S. Ser. No. 10/209,001 filed 30 Jul. 2002 now U.S. Pat. No. 6,987,102, which claims priority under 35 U.S.C. § 119(e) to U.S. provisional application Ser. No. 60/309,196 filed 31 Jul. 2001 and U.S. provisional application Ser. No. 60/382,155 filed 20 May 2002. The contents of these applications are incorporated herein by reference.

TECHNICAL FIELD

The invention is in the field of therapeutics and medicinal chemistry. More particularly, the invention concerns methods to mobilize progenitor/stem cells in subjects by administering certain polyamines.

BACKGROUND ART

Blood cells play a crucial part in maintaining the health and viability of animals, including humans. White blood cells include neutrophils, macrophage, eosinophils and basophils/mast cells as well the B and T cells of the immune system. White blood cells are continuously replaced via the hematopoietic system, by the action of colony stimulating factors (CSF) and various cytokines on stem cells and progenitor cells in hematopoietic tissues. The nucleotide sequences encoding a number of these growth factors have been cloned and sequenced. Perhaps the most widely known of these is granulocyte colony stimulating factor (G-CSF) which has been approved for use in counteracting the negative effects of chemotherapy by stimulating the production of white blood cells and progenitor cells (peripheral blood stem cell mobilization). A discussion of the hematopoietic effects of this factor can be found, for example, in U.S. Pat. No. 5,582,823, incorporated herein by reference.

Several other factors have been reported to increase white blood cells and progenitor cells in both human and animal subjects. These agents include granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin and growth related oncogene, as single agents or in combination (Dale, D., et al., *Am. J of Hematol.* (1998) 57:7–15; Rosenfeld, C., et al., *Bone Marrow Transplantation* (1997) 17:179–183; Pruijt, J., et al., *Cur. Op. in Hematol.* (1999) 6:152–158; Broxmeyer, H., et al., *Exp. Hematol.* (1995) 23:335–340; Broxmeyer, et al., *Blood Cells, Molecules and Diseases* (1998) 24:14–30; Glaspy, J., et al., *Cancer Chemother. Pharmacol.* (1996) 38 (suppl): S53–S57; Vadhan-Raj, S., et al., *Ann. Intern. Med.* (1997) 126:673–81; King, A., et al., *Blood* (2001) 97:1534–1542; Glaspy, J., et al., *Blood* (1997) 90:2939–2951).

While endogenous growth factors are pharmacologically effective, the well known disadvantages of employing proteins and peptides as pharmaceuticals underlies the need to add to the repertoire of such growth factors with agents that are small molecules. In another aspect, such small molecules are advantageous over proteins and peptides where production in large quantities are desired.

A number of cyclic polyamine antiviral agents have been described in a series of U.S. patents and applications over the last several years. These patents, U.S. Pat. Nos. 5,021,409; 6,001,826; 5,583,131; 5,698,546; and 5,817,807 are incorporated herein by reference. Also incorporated by reference are PCT publications WO 00/02870 based on an application filed 8 Jul. 1998 and WO 01/44229, based on an application filed 17 Dec. 1999, which describe additional compounds. These publications describe the structural characteristics of the cyclic polyamine antiviral agents.

The structural characteristics of a number of non-cyclic amine antiviral agents have also been described in a series of U.S. applications, now published as PCT publications. These publications, WO 00/56729, based on an application filed 24 Mar. 2000; WO 02/22600, based on applications filed 15 and 20 Sep. 2000; WO 02/22599, based on applications filed 15 and 22 Sep. 2000 as well as WO 02/34745 published 2 May 2002, are incorporated herein by reference in their entirety.

In addition, improved methods for preparation of some of the cyclic polyamine compounds are described in U.S. Patent Nos. 5,612,478; 5,756,728; 5,801,281; and 5,606,053 and PCT publication WO 02/26721, based on an application filed 29 Sep. 2000. The disclosures of these U.S. documents are also incorporated herein by reference in their entirety.

We have previously found, and have disclosed in PCT publication WO 02/58653, based on an application filed 1 Feb. 2000, that some of the polyamine antiviral agents described in the above mentioned publications have the effect of increasing the white blood cell count. It has now been found that the polyamine antiviral agents described in the above-mentioned publications also have the effect of increasing progenitor cells and/or stem cells.

The development and maturation of blood cells is a complex process. Mature blood cells are derived from hematopoietic precursor cells (progenitor) cells and stem cells present in specific hematopoietic tissues including bone marrow. Within these environments hematopoietic cells proliferate and differentiate prior to entering the circulation. The chemokine receptor CXCR4 and its natural ligand stromal cell derived factor-1 (SDF-1) appear to be important in this process (for reviews see Maekawa, T., et al, *Internal Med.* (2000) 39:90–100; Nagasawa, T., et al., *Int. J Hematol.* (2000) 72:408–411). This is demonstrated by reports that CXCR4 or SDF-1 knock-out mice exhibit hematopoietic defects (Ma, Q., et al., *Proc. Natl. Acad. Sci USA* (1998) 95:9448–9453; Tachibana, K., et al., *Nature* (1998) 393: 591–594; Zou, Y-R., et al., *Nature* (1998) 393:595–599). It is also known that CD34+ progenitor cells express CXCR4 and require SDF-1 produced by bone marrow stromal cells for chemoattraction and engraftment (Peled, A., et al., *Science* (1999) 283:845–848) and that in vitro, SDF-1 is chemotactic for both CD34+ cells (Aiuti, A., et al., *J Exp. Med.* (1997) 185:111–120; Viardot, A., et al., *Ann. Hematol.* (1998) 77:194–197) and for progenitor/stem cells (Jo, D-Y., et al., *J Clin. Invest.* (2000) 105:101–111). SDF-1 is also an important chemoattractant, signaling via the CXCR4 receptor, for several other more committed progenitors and mature blood cells including T-lymphocytes and monocytes (Bleul, C., et al., *J Exp. Med.* (1996) 184:1101–1109), pro-and pre-B lymphocytes (Fedyk, E. R., et al., *J Leukoc. Biol.* (1999) 66:667–673; Ma, Q., et al., *Immunity* (1999) 10:463–471) and megakaryocytes (Hodohara, K., et al., *Blood* (2000) 95:769–775; Riviere, C., et al., *Blood* (1999) 95:1511–1523; Majka, M., et al., *Blood* (2000) 96:4142–4151; Gear, A., et al., *Blood* (2001) 97:937–945; Abi-Younes, S., et al., *Circ. Res.* (2000) 86:131–138).

Thus, in summary, it appears that SDF-1 is able to control the positioning and differentiation of cells bearing CXCR4 receptors whether these cells are stem cells (i.e., cells which are CD34+) and/or progenitor cells (which result in formation of specified types of colonies in response to particular stimuli; that can be CD34⁺ or CD34⁻) or cells that are somewhat more differentiated.

Recently, considerable attention has been focused on the number of CD34+ cells mobilized in the pool of peripheral blood progenitor cells used for autologous stem cell transplantation. The CD34+ population is the component thought to be primarily responsible for the improved recovery time after chemotherapy and the cells most likely responsible for long-term engraftment and restoration of hematopoiesis (Croop, J. M., et al., *Bone Marrow Transplantation* (2000) 26:1271–1279). The mechanism by which CD34+ cells re-engraft may be due to the chemotactic effects of SDF-1 on CXCR4 expressing cells (Voermans, C. *Blood*, 2001, 97, 799–804; Ponomaryov, T., et al., *J Clin. Invest.* (2000) 106:1331–1339). More recently, adult hematopoietic stem cells were shown to be capable of restoring damaged cardiac tissue in mice (Jackson, K., et al., *J Clin. Invest.* (2001) 107:1395–1402; Kocher, A., et al., *Nature Med.* (2001) 7:430–436).

Thus, the role of the CXCR4 receptor in managing cell positioning and differentiation has assumed considerable significance.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

DISCLOSURE OF THE INVENTION

The invention is directed to methods of treating animal subjects, in particular, veterinary and human subjects, to enhance the number of progenitor cells and/or stem cells. The progenitor and/or stem cells may be harvested and used in cell transplantation. The methods of the invention employ polyamines including those described in the patents and publications incorporated hereinabove by reference.

In one aspect, therefore, the invention is directed to a method to elevate the progenitor cells and/or stem cells, in a subject, which method comprises administering to said subject an amount of a compound of formula (1) or of a pharmaceutical composition thereof effective to elevate progenitor cell and/or stem cell levels. In one embodiment, bone marrow progenitor and/or stem cells are mobilized for myocardial repair.

The methods of the invention also include treatment of cell populations ex vivo with the compounds of formula (1) and introducing the treated populations into a compatible subject. The compounds of formula (1) may be used alone or in combination with other compounds and compositions to enhance the population of stem cells and/or progenitor cells in the peripheral blood. An enhanced production of white blood cells in the bone marrow may result as well.

In additional aspects, the invention is directed to pharmaceutical compositions containing the compound of formula (1) for use in effecting an elevation of progenitor cells and/or stem cells in animal subjects.

The compounds of formula (1) are of the formula:

Z-linker-Z'     (1)

wherein Z is a cyclic polyamine containing 9–32 ring members of which 2–8 are nitrogen atoms, said nitrogen atoms separated from each other by at least 2 carbon atoms, and wherein said heterocycle may optionally contain additional heteroatoms besides nitrogen and/or may be fused to an additional ring system;

or Z is of the formula $$\begin{array}{c} A \\ \diagdown \\ N- \\ \diagup \\ B \end{array}$$

wherein A comprises a monocyclic or bicyclic fused ring system containing at least one N and B is H or an organic moiety of 1–20 atoms;

Z' may be embodied in a form as defined by Z above, or alternatively may be of the formula —N(R)—(CR$_2$)$_n$—X wherein each R is independently H or straight, branched or cyclic alkyl (1–6C), n is 1 or 2, and X is an aromatic ring, including heteroaromatic rings, or is a mercaptan;

or Z$^1$ is of the formula —Ar(Y)$_j$;

wherein Ar is an aromatic or heteroaromatic moiety, and each Y is independently a non-interfering substituent and j is 0–3;

"linker" represents a bond, alkylene (1–6C) or may comprise aryl, fused aryl, oxygen atoms contained in an alkylene chain, or may contain keto groups or nitrogen or sulfur atoms.

Particularly preferred forms of the compounds useful in the invention are of the formula:

(2)

$$(R^1)_k \underset{N}{\underbrace{\phantom{XXX}}} \overset{A}{\underset{}{\phantom{XX}}} )_l$$

$$(CR_2)_n^a$$

$$N—(CR_2)_n—Ar—(Y)_j$$

$$(CR_2)_n^b$$

$$\underset{R^2}{\overset{X=}{\underset{E}{\phantom{X}}}} \underset{R^3}{\overset{}{\underset{N}{\phantom{X}}}}$$

and salts and prodrug forms thereof wherein:

Ring A optionally comprises a heteroatom selected from N, O and S;

the dotted lines represent optional unsaturation;

R1, R2 and R3 are non-interfering substituents;

k is 0–4;

l is 0, 1, or 2;

X is unsubstituted or substituted C or N; or is O or S;

Ar is the residue of an aromatic or heteroarmatic moiety;

each n is independently 0–2;

each R is independently H or alkyl (1–6C);

j is 0–3; and each Y is independently halo, OH, SH, SO, $SO_2$, or an organic moiety of 1–20C atoms that does not contain N wherein two such Y may be connected to form a fused ring wth Ar, or is selected from the group consisting of
—$(CR_2)_m CN$,
—$(CR_2)_m NR^5{}_2$,
—$(CR_2)_m NR(CR_2)_m NRR_4$,
—$(CR_2)_m NR(CR_2)_m NR(CR_2)_m NR^5{}_2$,
—$(CR_2)_m CO(CR_2)_m NR^5{}_2$,
—$(CR_2)_m CO(CR_2)_m NR(CR_2)_m NRR^4$,
—$(CR_2)_m CO(CR_2) NR(CR_2)_m NR(CR_2)_m NR^5{}_2$,
—$(CR_2)_m NRCO(CR_2)_m NRR^4$,
—$(CR_2)_m NRCO(CR_2)_m NR(CR_2)_m NR^5{}_2$,
—$(CR_2)_m NRCO(CR_2)_m NR(CR_2)_m NR(CR_2)_m NR(CR_2)_m NR^5{}_2$,
—$CH=N-Z''$,
—$(CR_2)_m Z''$,
—$NR\,(CR_2)_m Z''$,
—$(CR_2)_m NROH$,
$(CR_2)_m CONROH$, and
$(CR_2)_m CR=NOH$, wherein Z" is an optionally substituted aromatic or heteroaromatic moiety containing 5–12 ring members; and wherein R is as defined above, each m is independently 0–4, and $R^4$ and each $R^5$ is independently H, alkyl (1–6C), alkenyl (1–6C), alkynyl (1–6C), or acyl (1–6C), each optionally substituted by one or more nonaromatic, nonheterocyclic substituent(s), and wherein two $R^5$ may be connected to form a cyclic amine, optionally containing one or more additional heteroatoms selected from N, O, and S.

MODES OF CARRYING OUT THE INVENTION

Figure 1:
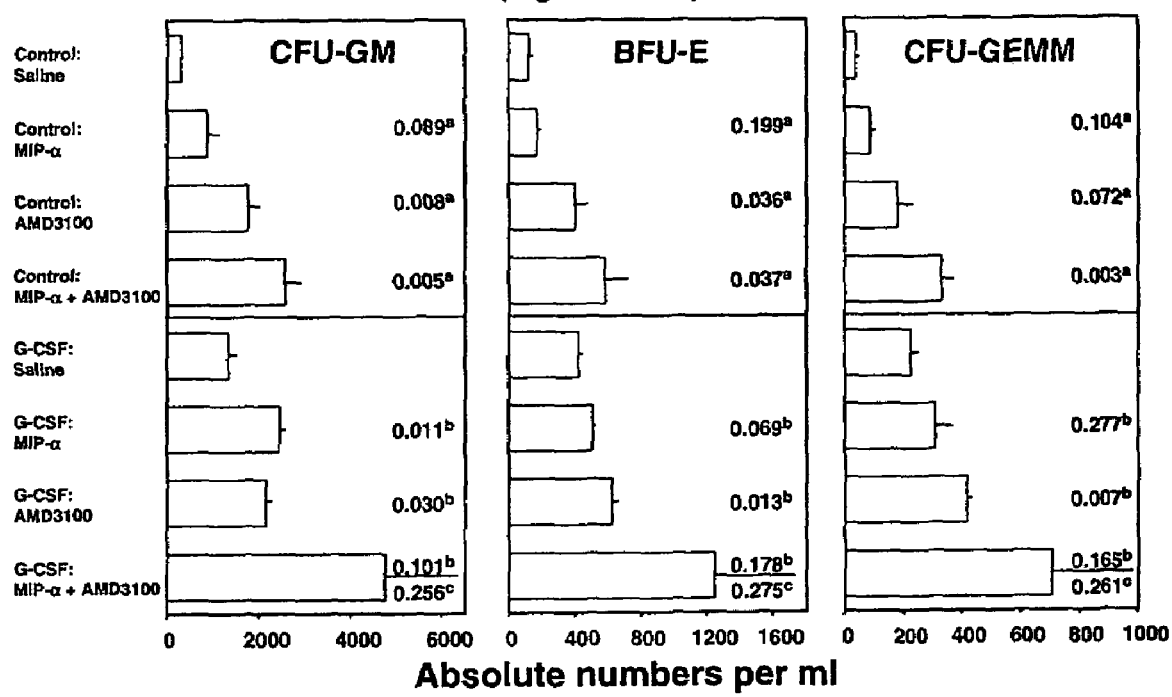
FIG. 1 shows a graph of obtaining myeloid progenitors in response to treatment with 1,1'-[1,4-phenylene-bis(methylene)]-bis-1,4,8,11-tetraazacyclotetradecane (AMD3100) in combination with macrophage inflammatory protein after administration of G-CSF.

The compounds useful in the invention are of the general formula set forth as formula (1) above. Certain embodiments are preferred; included among these are the compounds set forth in the above-incorporated U.S. patents and other patent documents.

The cyclic polyamine and non-cyclic amine antiviral agents described in the above-mentioned documents inhibit HIV replication via inhibition of CXCR4, the co-receptor required for fuision and entry of T-tropic HIV strains, and also inhibit the binding and signaling induced by the natural ligand, the chemokine SDF-1. While not wishing to be bound by any theory, the compounds of formula (1) which inhibit the binding of SDF-1 to CXCR4 effect an increase in stem and/or progenitor cells by virtue of such inhibition. Enhancing the stem and/or progenitor cells in blood is helpful in treatments to alleviate the effects of protocols that adversely affect the bone marrow, such as those that result in leukopenia. These are known side-effects of chemotherapy and radiotherapy. The compounds of formula (1) also enhance the success of bone marrow transplantation, enhance wound healing and burn treatment, and aid in restoration of damaged organ tissue. They also combat bacterial infections that are prevalent in leukemia. The compounds of formula (1) are used to mobilize and harvest CD34+ cells via apheresis with and without combinations with other mobilizing factors. The harvested cells are used in treatments requiring stem cell transplantations.

As used herein, the term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols.

As used herein, "stem" cells are less differentiated forms of progenitor cells. Typically, such cells are often positive for CD34. Some stem cells do not contain this marker, however. These CD34+ cells can be assayed using fluorescence activated cell sorting (FACS) and thus their presence can be assessed in a sample using this technique.

In general, CD34+ cells are present only in low levels in the blood, but are present in large numbers in bone marrow. While other types of cells such as endothelial cells and mast cells also may exhibit this marker, CD34 is considered an index of stem cell presence.

In general, in compounds of formula (1), preferred embodiments of Z and Z' are cyclic polyamine moieties having from 9–24C that include 3–5 nitrogen atoms. Particularly preferred are 1,5,9,13-tetraazacyclohexadecane; 1,5,8,11,14-pentaazacyclohexadecane; 1,4,8,11-tetraazacylotetradecane; 1,5,9-triazacyclododecane; 1,4,7,10-tetraazacyclododecane; and the like, including such cyclic polyamines which are fused to an additional aromatic or heteroaromatic rings and/or containing a heteroatom other than nitrogen incorporated in the ring. Embodiments wherein the cyclic polyamine contains a fused additional cyclic system or one or more additional heteroatoms are described in U.S. Pat. No. 5,698,546 and WO 01/44229 incorporated hereinabove by reference. Also preferred are 3,7,11,17-tetraazabicyclo(13.3.1)heptadeca-1(17),13,15-triene;

4,7,10,17-tetraazabicyclo(13.3.1)heptadeca-1(17),13,15-triene;

1,4,7,10-tetraazacyclotetradecane; 1,4,7-triazacyclotetradecane; and 4,7,10-triazabicyclo(13.3.1)heptadeca-1(17),13,15-triene.

When Z' is other than a cyclic polyamine as defined in Z, its preferred embodiments are set forth in U.S. Pat. No. 5,817,807, also incorporated herein by reference.

Preferred forms where
Z is of the formula

wherein A comprises a monocyclic or bicyclic fused ring system containing at least one N and B is H or an organic moiety of 1–20 atoms are disclosed in WO 00/56729; WO 02/22600; WO 02/34745; and WO 02/22599 cited above and all incorporated herein by reference.

In particular, in one embodiment, the compounds include those of formula (2) wherein each R is independently straight or branched chain alkyl or may be cyclic, and may optionally be substituted by 1–2 substituents selected from halo, hydroxy and alkoxy. Preferably each R is H or lower straight-chain alkyl (1–4C), preferably methyl.

Ar is the residue of an aromatic or heteroaromatic moiety which contains a single or fused ring system and containing 5–6 ring members in the monocyclic system and 9–12 members in the fused ring system. The residue may be optionally substituted. Examples of optionally substituted aromatic and heteroaromatic groups include benzene, naphthalene, dihydronaphthalene, tetrahydronaphthalene, pyridine, quinoline, isoquinoline, imidazole, benzimidazole, azabenzimidazole, benzotriazole, furan, benzofuran, thiazole, benzothiazole, oxazole, benzoxazole, pyrrole, indole, imidazole, tetrahydroquinoline, tetrahydroisoquinoline, pyrazole, thiophene, isoxazole, isothiazole, triazole, tetrazole, oxadiazole, thiadiazole, imidazoline, and benzopyran. Oxides of the nitrogen and sulfur containing heteroaromatic rings are also included in the present invention. Particularly preferred forms of Ar are phenylene, pyridylene or pyridinylene.

When compounds of formula (2) contain elements that are "optionally substituted" these substituents are preferably halogen, nitro, cyano, carboxylic acid, optionally substituted alkyl, alkenyl or cycloalkyl groups, an optionally substituted hydroxyl group, an optionally substituted thiol group, an optionally substituted amino, an optionally substitute acyl group, an optionally substituted carboxylate, carbamate, carboxamide or sulfonamide group, or an optionally substituted aromatic or heterocyclic group.

Examples of halogen include fluorine, chlorine, bromine, iodine, etc., with fluorine and chlorine preferred.

Examples of optionally substituted alkyl include $C_{1-10}$ alkyl, including methyl, ethyl propyl, etc.; examples of optionally substituted alkenyl groups include $C_{2-10}$ alkenyl such as allyl, crotyl, 2-pentenyl, 3-hexenyl, etc.; and examples of optionally substituted cycloalkyl groups include $C_{3-10}$ cycloalkyl such as cyclopropyl, cyclobutyl, cyclopentyl, cyclohexyl, cycloheptyl, etc. In these cases, $C_{1-6}$ alkyl, alkenyl and cycloalkyl are preferred. The optional substituent may also be an optionally substituted aralkyl (e.g., phenyl $C_{1-4}$ alkyl) or heteroalkyl for example, phenylmethyl (benzyl), phenylethyl, pyridinylmethy, pyridinylethyl, etc. The heterocyclic group may be a 5 or 6 membered ring containing 1–4 heteroatoms.

Examples of optionally substituted hydroxyl and thiol groups include those wherein the substituent is an optionally substituted alkyl (e.g., $C_{1-10}$ alkyl) such as methyl, ethyl, propyl, isopropyl, butyl, isobutyl, sec-butyl, tert-butyl, pentyl, etc., preferably ($C_{1-6}$) alkyl; an optionally substituted cycloalkyl (e.g., $C_{3-7}$ cycloalkyl, etc., such as cyclopropyl, cyclobutyl, cyclopentyl, cyclohexyl, cycloheptyl, etc.); an optionally substituted aralkyl (e.g., phenyl-$C_{1-4}$ alkyl, e.g., benzyl, phenethyl, etc.). Where there are two adjacent hydroxyl or thiol substituents, the heteroatoms may be connected via an alkylene group such as $O(CH_2)_nO$ and $S(CH_2)_nS$ (where n=1–5). Examples include methylenedioxy, ethylenedioxy, etc. Oxides of thio-ether groups such as sulfoxides and sulfones are also encompassed.

Further examples of the optionally substituted hydroxyl group include an optionally substituted $C_{2-4}$ alkanoyl (e.g., acetyl, propionyl, butyryl, isobutyryl, etc.), $C_{1-4}$ alkylsufonyl (e.g., methanesulfonyl, ethanesulfonyl, etc.) and an optionally substituted aromatic and heterocyclic carbonyl group including benzoyl, pyridinecarbonyl, etc.

The substituents on optionally substituted amino group may bind to each other to form a cyclic amino group (e.g., 5- to 6-membered cyclic amino, etc., such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g., fluorine, chlorine, bromine, iodine, etc.), nitro, cyano, hydroxy group, thiol group, amino group, carboxyl group, an optionally halogenated $C_{1-4}$ alkyl (e.g., trifluoromethyl, methyl, ethyl, etc.), an optionally halogenated $C_{1-4}$ alkoxy (e.g., methoxy, ethoxy, trifluoromethoxy, trifluoroethoxy, etc.), $C_{2-4}$ alkanoyl (e.g., acetyl, propionyl, etc.), $C_{1-4}$ alkylsulfonyl (e.g., methanesulfonyl, ethanesulfonyl, etc.) the number of preferred substituents are 1 to 3.

The amino group may also be substituted once or twice (to form a secondary or tertiary amine) with a group such as an optionally substituted alkyl group including $C_{1-10}$ alkyl (e.g., methyl, ethyl propyl, etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g., phenyl $C_{1-4}$ alkyl) or heteroalkyl for example, phenyl, pyridine, phenylmethyl (benzyl), phenethyl, pyridinylmethyl, pyridinylethyl, etc. The heterocyclic group may be a 5 or 6 membered ring containing 1–4 heteroatoms. The optional substituents of the "optionally substituted amino groups are the same as defined above for the "optionally substituted cyclic amino group."

The amino group may be substituted with an optionally substituted $C_{2-4}$ alkanoyl, e.g., acetyl, propionyl, butyryl, isobutyryl etc., or a $C_{1-4}$ alkylsulfonyl (e.g., methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl, etc. The heterocycles are as defined above.

Examples of the optionally substituted acyl groups include a carbonyl group or a sulfinyl or sulfonyl group binding to hydrogen; or to an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.; an optionally substituted cycloalkyl (e.g., $C_{3-7}$ cycloalkyl, etc., such as cyclopropyl, cyclobutyl, cyclopentyl, cyclohexyl, cycloheptyl, etc.); an optionally substituted alkenyl (e.g., $C_{2-10}$ alkenyl such as allyl, crotyl, 2-pentenyl, etc., preferably lower ($C_{2-6}$) alkenyl, etc.); an optionally substituted cycloalkenyl (e.g., $C_{3-7}$ cycloalkenyl, etc., such as 2-cyclopentenyl, 2-cyclohexenyl, 2-cyclopentenylmethyl, 2-cyclohexenylmethyl, etc.) an optionally substituted 5- to 6-membered monocyclic aromatic group (e.g., phenyl, pyridyl, etc.).

Examples of the optionally substituted carboxylate group (ester groups) include an optionally substituted alkyl (e.g., $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower ($C_{1-6}$) alkyl, etc.); an optionally substituted cycloalkyl, e.g., $C_{3-7}$ cycloalkyl, etc. such as cyclopropyl, cyclobutyl, cyclopentyl, cyclohexyl, cycloheptyl, etc.); an optionally substituted alkenyl (e.g., $C_{2-10}$ alkenyl such as allyl, crotyl, 2-pentenyl, 3-hexenyl, etc., preferably lower ($C_{2-6}$) alkenyl, etc.); an optionally substituted cycloalkenyl e.g., $C_{3-7}$ cycloalkenyl, etc., such as 2-cyclohexenylmethyl, etc.); an optionally substituted aryl e.g., phenyl, naphthyl, etc.) and $C_{1-4}$ aryl for example, benzyl, phenethyl etc. Groups such as methoxymethyl, methoxyethyl, etc., are also encompassed.

Examples of the optionally substituted carboxamide and sulfonamide groups are identical in terms of the amine definition as the "optionally substituted amino group" defined above.

Examples of the optionally substituted aromatic or heterocyclic groups are phenyl, naphthyl, or a 5- or 6-membered heterocyclic ring containing 1–4 heteroatoms. The optional substituents are essentially identical to those listed above.

The non-interfering substituents $R^1$, $R^2$ and $R^3$ are similar to those set forth as "optional substituents". Preferably, $R^1$ is selected from the optional substituents set forth above, preferably halo, substituted or unsubstituted alkyl, substituted or unsubstituted hydroxyl, substituted or unsubstituted amino, substituted or unsubstituted thiol, and substituted or unsubstituted acyl. Preferably k is 0–2, preferably 0–1, and more preferably 0.

The substituents $R^2$ and $R^3$ are preferably selected from the preferred embodiments of $R^1$ listed immediately above, or, more preferably, may be joined to form a saturated or unsaturated ring system, preferably a benzo ring system.

In the above formula 2, examples of the optionally substituted ring system containing ring A are dihydroquinoline, tetrahydroquinoline, pyranopyridine, dihydropyranopyridine, thiapyranopyridine, dihydrothiapyranopyridine, dihydronaphthyridine, tetrahydronaphthyridine. Oxides of sulfur-containing heterocycles are also encompassed in the present invention. In the above ring system containing Ring A, the optional nitrogen atom may be substituted with hydrogen, a substituted alkyl, alkenyl, cycloalkyl or aryl group, or may be the nitrogen atom of a carboxamide, carbamate or sulfonamide. Preferred for l is l=1, it is preferred that ring A be saturated. The most preferred combination is tetrahydroquinoline.

In the above formula 2, X may be CH (pyrrole), O (oxazole), S (thiazole), NH or NR (imidazole) where R is a $C_{1-6}$ alkyl group or acyl, sulfonyl group. In Formula 1, two adjacent $R^1$ and/or $R^2$ and $R^3$ may be joined to form an optionally substituted, fused 5–7 membered ring. Examples of fused ring systems include but are not limited to indole, tetrahydroindole, benzimidazole, tetrahydrobenzimidazole, azabenzimidazole, benzoxazole, tetrahydrobenzoxazole, benzothiazole, tetrahydrobenzothiazole. The preferred ring systems resulting from $R^2$ and $R^3$ include those which result in benzothiazole and benzoimidazole.

In the compounds of formula 2, it is preferred that one of the $(CR_2)_n$ linkers between the ring system containing ring A and ring E is that wherein n is 0, i.e., the linkage is merely a covalent bond. Also preferred embodiments of $(CR_2)_n$ in this context are ethylene or methylene, preferably methylene. In the most preferred embodiments, the linkage between the nitrogen shown in formula 2 and ring A is a bond and that between the nitrogen shown and ring E is $CH_2$. As shown, ring E may be coupled to the linker through any position, but preferably through position 2, 4 or 5, most preferably through position 2.

In the compounds of formula 2, preferred values of j are 0–2, preferably 1–2. The embodiments of Y may be varied widely provided Y does not contain nitrogen. Thus, Y may be halo, OH, SH, SO, $SO_2$ and the like, or a substituent of 1–20 carbons, optionally containing as a substitution, for one or more said carbons, a heteroatom such as O or S. Preferred embodiments wherein N is not present in Y include halo, optionally substituted alkyl, optionally substituted hydroxyl, optionally substituted thiol, and optionally substituted carboxylate, and a saturated or unsaturated ring. These substituents are described above. Where N is included in Y, Y is selected from the moieties set forth hereinabove. In these substituents, Z" is an aromatic or heteroaromatic moiety containing 5–12 ring members. Thus, Y may include a single or fused ring. Examples of preferred forms of Z" are identical to those set forth with regard to the aromatic residue Ar set forth above, but are monovalent.

As shown, in certain embodiments, R, defined as H or alkyl (1–6C), is replaced by $R^4$ or $R^5$ which have a broader definitions and can include the embodiments of R as well as embodying optionally substituted alkenyl, acyl, and the like as set forth above. Preferred forms of $R^4$ and $R^5$ include those typified by R and optionally substituted alkenyl. Also preferred are embodiments where two $R^5$ are connected to form a cyclic amine, including those which contain one or more additional heteroatoms such as N, O and/or S.

Preferred forms of Y when Y contains N are those wherein R is in all cases H or methyl, preferably H and those where two $R^5$ are coupled. Especially preferred are those of the formula —$(CR_2)_m CN$,
—$(CR_2)_m NR^5{}_2$,
—$(CR_2)_m NR(CR_2)_m NRR^4$,
—$(CR_2)_m CO(CR_2)_m NR^5{}_2$,
—$(CR_2)_m Z''$, and
—$NR(CR_2)_m Z''$, and those wherein Y comprises guanidino or NHNHR, especially wherein $(CR_2)_m$ is $CH_2$, $CH_2CH_2$, or $CH_2CH_2CH_2$, or wherein m is 0, and those wherein $R^4$ or $R^5$ is H or is lower alkyl, alkenyl, or hydrogen, or wherein both $R^5$ are identical.

Particularly preferred are —$CH_2NH_2$, $CH_2CH_2NH_2$, —$CH_2NMe_2$, —$CH_2CH_2NMe_2$, —$CONH_2$, —$CONMe_2$, and the like.

Preferred Z" are optionally substituted residues of benzene, oxazole, imidazole, thiazole, benzimidazole, benzthiazole, benzoxazole, indole, thiophene, tetrazine, pyrimidine, pyridine, and the like.

Preferred forms of the linker moiety include those wherein the linker is a bond, or wherein the linker includes an aromatic moiety flanked by alkylene, preferably methylene moieties. Preferred linking groups include the methylene bracketed forms of 1,3-phenylene, 2,6-pyridine, 3,5-pyridine, 2,5-thiophene, 4,4'-(2,2'-bipyrimidine); 2,9-(1,10-phenanthroline) and the like. A particularly preferred linker is 1,4-phenylene-bis-(methylene).

Particularly preferred embodiments of the compound of the formula (1) include 2,2'-bicyclam; 6,6'-bicyclam; the embodiments set forth in U.S. Pat. Nos. 5,021,409, and 6,001,826, and in particular 1,1'-[1,4-phenylene-bis(methylene)]-bis-1,4,8,11-tetraazacyclotetradecane, set forth in U.S. Pat. No. 5,583,131, and designated herein AMD3100.

Other preferred embodiments include
N-[1,4,8,11-tetraazacyclotetradecanyl-1,4-phenylenebis(methylene)]-2-aminomethyl)pyridine;
7,7'-[1,4-phenylenebis(methylene)]bis-4,7,10,17-tetraazabicyclo-[13.3.1]heptadeca-1(17),13,15-triene;
7,7'-[1,4-phenylenebis(methylene)]bis-3,7,11,17-tetraazabicyclo[13.3.1]heptadeca-1(17),13,15-triene;
1,1'-[1,3-phenylenebis(methylene)]-bis-1,4,8,11-tetraazacyclotetradecane;
1,1'-[1,4-phenylenebis(methylene)]-bis-1,4,8,11-tetraazacyclotetradecane;
1,1'-[1,4-phenylene-bis-(methylene)]-bis-1,4,7,10-tetraazacyclotetradecane;

1,1'-[1,3-phenylene-bis-(methylene)]-bis-1,4,7,10-tetraazacyclotetradecane;
11,11'-(1,2-propanediyl)bis-1,4,8,11-tetraazacyclotetradecane;
N-[4-(1,4,7-triazacyclotetra-decane)-1,4-phenylenebis(methylene)]-2-(aminomethyl)pyridine;
N-[7-(4,7,10-triazabicyclo[13.3.1]heptadeca-1(17),13,15-triene)-1,4-phenylenebis(methylene)]-2-(aminomethyl)pyridine;
N-[7-(4,7,10,17-tetraazabicyclo[13.3.1]heptadeca-1(17),13,15-triene)-1,4-phenylenebis(methylene)]-2-(aminomethyl)pyridine;
N-[4-[4,7,10,17-tetraazabicyclo[13.3.1]heptadeca-1(17),13,15-triene]-1,4-phenylenebis(methylene)]-2-(aminomethyl)pyridine;
3,3'-(bis-1,5,9,13-tetraazacyclohexadecane);
3,3'-(bis-1,5,8,11,14-pentaazacyclohexadecane), methylene (or polymethylene) di-1-N-1,4,8,11-tetraazacyclotetradecane;
3,3'-bis-1,5,9,13,-tetraazacyclohexadecane;
3,3'-bis-1,5,8,11,14-pentaazacyclohexadecane;
5,5'-bis-1,4,8,11-tetraazacyclotetradecane;
2,5'-bis-1,4,8,11-tetraazacyclotetradecane;
2,6'-bis-1,4,8,11-tetraazacyclotetradecane;
11,11'-(1,2-ethanediyl)bis-1,4,8,11-tetraazacyclotetradecane;
11,11'-(1,2-propanediyl)bis-1,4,8,11-tetraazacyclotetradecane;
11,11'-(1,2-butanediyl)bis-1,4,8,11-tetraazacyclotetradecane;
11,11'-(1,2-pentanediyl)bis-1,4,8,11-tetraazacyclotetradecane;
11,11'-(1,2-hexanediyl)bis-1,4,8,11-tetraazacyclotetradecane;
3,3'-bis-1,5,9,13-tetraazacyclohexadecane;
3,3'-bis-1,5,8,11,14-pentaazacyclohexadecane;
5,5'-bis-1,4,8,11-tetraazacyclotetradecane;
2,5'-bis-1,4,8,11-tetraazacyclotetradecane;
2,6'-bis-1,4,8,11-tetraazacyclotetradecane;
11,11'-(1,2-ethanediyl)bis-1,4,8,11-tetraazacyclotetradecane;
11,11'-(1,2-propanediyl)bis-1,4,8,11-tetraazacyclotetradecane;
11,11'-(1,2-butanediyl)bis-1,4,8,11-tetraazacyclotetradecane;
11,11'-(1,2-pentanediyl)bis-1,4,8,11-tetraazacyclotetradecane;
11,11'-(1,2-hexanediyl)bis-1,4,8,11-tetraazacyclotetradecane;
1,1'-[1,3-phenylenebis(methylene)]-bis-1,4,8,11-tetraazacyclotetradecane;
1,1'-[1,4-phenylenebis(methylene)]-bis-1,4,8,11-tetraazacyclotetradecane;
1,1'-[3,3'-biphenylene-bis-(methylene)]-bis-1,4,8,11-tetraazacyclotetradecane;
11,11'-[1,4-phenylene-bis-(methylene)]-bis-1,4,7,11-tetraazacyclotetradecane;
1,11'-[1,4-phenylene-bis(methylene)]-1,4,8,11-tetraazacyclotetradecane;
1,1'-[2,6-pyridine-bis-(methylene)]-bis-1,4,8,11-tetraazacyclotetradecane;
1,1-[3,5-pyridine-bis-(methylene)]-bis-1,4,8,11-tetraazacyclotetradecane;
1,1'-[2,5-thiophene-bis-(methylene)]-bis-1,4,8,11-tetraazacyclotetradecane;
1,1'-[4,4'-(2,2'-bipyridine)-bis-(methylene)]-bis-1,4,8,11-tetraazacyclotetradecane;
1,1'-[2,9-(1,10-phenanthroline)-bis-(methylene)]-bis-1,4,8,11-tetraazacyclotetradecane;
1,1'-[1,3-phenylene-bis-(methylene)]-bis-1,4,7,10-tetraazacyclotetradecane;
1,1'-[1,4-phenylene-bis-(methylene)]-bis-1,4,7,10-tetraazacyclotetradecane;
1,1'-[5-nitro-1,3-phenylenebis(methylene)]bis-1,4,8,11-tetraazacyclotetradecane;
1,1'-[2,4,5,6-tetrachloro-1,3-phenyleneis(methylene)]bis-1,4,8,1 1-tetraazacyclotetradecane;
1,1'-[2,3,5,6-tetrafluoro-1,4-phenylenebis(methylene)]bis-1,4,8,11-tetraazacyclotetradecane;
1,1'-[1,4-naphthylene-bis-(methylene)]bis-1,4,8,11-tetraazacyclotetradecane;
1,1'-[1,3-phenylenebis-(methylene)]bis-1,5,9-triazacyclododecane;
1,1'-[1,4-phenylene-bis-(methylene)]-1,5,9-triazacyclododecane;
1,1'-[2,5-dimethyl-1,4-phenylenebis-(methylene)]-bis-1,4,8,11-tetraazacyclotetradecane;
1,1'-[2,5-dichloro-1,4-phenylenebis-(methylene)]-bis-1,4,8,11-tetraazacyclotetradecane;
1,1'-[2-bromo-1,4-phenylenebis(methylene)]-bis-1,4,8,11-tetraazacyclotetradecane;
1,1'-[6-phenyl-2,4-pyridinebis-(methylene)]-bis-1,4,8,11-tetraazacyclotetradecane;
7,7'-[1,4-phenylene-bis(methylene)]bis-3,7,11,17-tetraazabicyclo[13.3.1]heptadeca-1(17),13,15-triene;
7,7'-[1,4-phenylene-bis(methylene)]bis[15-chloro-3,7,11,17-tetraazabicyclo[13.3.1]heptadeca-1(17),13,15-triene];
7,7'-[1,4-phenylene-bis(methylene)]bis[15-methoxy-3,7,11,17-tetraazabicyclo[13.3.1]heptadeca-1(17),13,15-triene];
7,7'-[1,4-phenylene-bis(methylene)]bis-3,7,11,17-tetraazabicyclo[13.3.1]-heptadeca-13,16-triene-15-one;
7,7'-[1,4-phenylene-bis(methylene)]bis-4,7,10,17-tetraazabicyclo[13.3.1]-heptadeca-1(17),13,15-triene;
8,8'-[1,4-phenylene-bis(methylene)]bis-4,8,12,19-tetraazabicyclo[15.3.1]nonadeca-1(19),15,17-triene;
6,6'-[1,4-phenylene-bis(methylene)]bis-3,6,9,15-tetraazabicyclo[11.3.1]pentadeca-1(15),11,13-triene;
6,6'-[1,3-phenylene-bis(methylene)]bis-3,6,9,15-tetraazabicyclo[1 3.1]pentadeca-1(15),11,13-triene;
17,17'-[1,4-phenylene-bis(methylene)]bis-3,6,14,17,23,24-hexaazatricyclo[17.3.1.1$^{8,12}$]tetracosa-1(23),8,10,12(24),19,21-hexaene;
N-[1,4,8,11-Tetraazacyclotetradecanyl-1,4-phenylenebis(methylene)]-2-(aminomethyl)pyridine;
N-[1,4,8,11-Tetraazacyclotetradecanyl-1,4-phenylenebis(methylene)]-N-methyl-2-(aminomethyl)pyridine;
N-[1,4,8,11-Tetraazacyclotetradecanyl-1,4-phenylenebis(methylene)]-4-(aminomethyl)pyridine;
N-[1,4,8,11-Tetraazacyclotetradecanyl-1,4-phenylenebis(methylene)]-3-(aminomethyl)pyridine;

N-[1,4,8,11-Tetraazacyclotetradecanyl-1,4-phenylenebis(methylene)]-(2-amino-methyl -5-methyl)pyrazine;
N-[1,4,8,11-Tetraazacyclotetradecanyl-1,4-phenylenebis(methylene)]-2-(aminoethyl)pyridine;
N-[1,4,8,11-Tetraazacyclotetradecanyl-1,4-phenylenebis(methylene)]-2-(aminomethyl)thiophene;
N-[1,4,8,11-Tetraazacyclotetradecanyl-1,4-phenylenebis(methylene)]-2-(aminoethyl)mercaptan;
N-[1,4,8,11-Tetraazacyclotetradecanyl-1,4-phenylenebis(methylene)]-2-amino-benzylamine;
N-[1,4,8,11-Tetraazacyclotetradecanyl-1,4-phenylenebis(methylene)]-4-amino-benzylamine;
N-[1,4,8,11-Tetraazacyclotetradecanyl-1,4-phenylenebis(methylene)]-4-(amino-ethyl)imidazole;
N-[1,4,8,11-Tetraazacyclotetradecanyl-1,4-phenylenebis(methylene)]-benzylamine;
N-[1,4,8,11-Tetraazacyclotetradecanyl-1,4-phenylenebis(methylene)]-purine;
N-[1,4,8,11-Tetraazacyclotetradecanyl-1,4-phenylenebis(methylene)]-4-phenylpiperazine;
N-[4-(1,4,7-Triazacyclotetra-decanyl)-1,4-phenylenebis(methylene)]-2-(aminomethyl)pyridine;
N-[7-(4,7,10,17-Tetraazabicyclo[13.3.1]heptadeca-1(17),13,15-trienyl)-1,4-phenylenebis(methylene)]-2-(aminomethyl)pyridine;
N-[7-(4,7,10-Triazabicyclo[13.3.1]heptadeca-1(17),13,15-trienyl)-1,4-phenylenebis(methylene)]-2-(aminomethyl)pyridine;
N-[4-[4,7,10-Triazabicyclo[13.3.1]heptadeca-1(17),13,15-trienyl]-1,4-phenylenebis(methylene)]-2-(aminomethyl)pyridine;
N-[1-(1,4,7-Triazacyclotetra-decanyl)-1,4-phenylenebis(methylene)]-2-(aminomethyl)pyridine;
N-[4-[4,7,10,17-Tetraazabicyclo[13.3.1]heptadeca-1(17),13,15-trienyl]-1,4-phenylenebis(methylene)]-2-(aminomethyl)pyridine;
N-[3-(3,6,17-Triazabicyclo[13.3.1]heptadeca-1(17),13,15-trienyl)-1,4-phenylenebis(methylene)]-2-(aminomethyl)pyridine;
N-[3-(3,6,17-Triazabicyclo[13.3.1]heptadeca-1(17),13,15-trienyl)-1,3-phenylenebis(methylene)]-2-(aminomethyl)pyridine;
N-[4-(4,7,17-Triazabicyclo[13.3.1]heptadeca-1(17),13,15-trienyl)-1,4-phenylenebis(methylene)]-2-(aminomethyl)pyridine;
N-[7-(4,7,17-Triazabicyclo[13.3.1]heptadeca-1(17),13,15-trienyl)-1,4-phenylenebis(methylene)]-2-(aminomethyl)pyridine;
N-[6-(3,6,9-Triazabicyclo[11.3.1]pentadeca-1(15),11,13-trienyl)-1,3-phenylenebis(methylene)]-2-(aminomethyl)pyridine;
N-[7-(4,10,17-Triazabicyclo[13.3.1]heptadeca-1(17),13,15-trienyl)-1,4-phenylenebis(methylene)]-2-(aminomethyl)pyridine;
N-[4-(1,7-Diazacyclotetradecanyl)-1,4-phenylenebis(methylene)]-2-(aminomethyl)pyridine;
N-[7-(4,10-Diazabicyclo[13.3.1]heptadeca-1(17),13,15-trienyl)-1,4-phenylenebis(methylene)]-2-(aminomethyl)pyridine;
N-[4-(11-Fluoro-1,4,7-triazacyclotetradecanyl)-1,4-phenylenebis(methylene)]-2-(aminomethyl)pyridine;
N-[4-(11,11-difluoro-1,4,7-triazacyclotetradecanyl)-1,4-phenylenebis(methylene)]-2-(aminomethyl)pyridine;
N-[4-(1,4,7-triazacyclotetradecan-2-one)-yl))-1,4-phenylenebis(methylene)]-2-(aminomethyl)pyridine;
N-[12-(5-oxa-1,9-diazacyclotetradecanyl)-1,4-phenylenebis(methylene)]-2-(aminomethyl)pyridine;
N-[4-(11-oxa-1,7-diazacyclotetradecanyl)-1,4-phenylenebis(methylene)]-2-(aminomethyl)pyridine;
N-[4-(11-thia-1,7-diazacyclotetradecanyl)-1,4-phenylenebis(methylene)]-2-(aminomethyl)pyridine;
N-[4-(11-sulfoxo-1,7-diazacyclotetradecanyl)-1,4-phenylenebis(methylene)]-2-(aminomethyl)pyridine;
N-[4-(1-sulfono-1,7-diazacyclotetradecanyl)-1,4-phenylenebis(methylene)]-2-(aminomethyl)pyridine;
N-[4-(1,4,7-triazacyclotetradecan-3-one)-yl))-1,4-phenylenebis(methylene)]-2-(aminomethyl)pyridine;
N-(2-pyridinylmethyl)-N'-(6,7,8,9-tetrahydro-5H-cyclohepta[b]pyridin-9-yl)-1,4-benzenedimethanamine;
N-(2-pyridinylmethyl)-N'-(5,6,7,8-tetrahydro-8-quinolinyl)-1,4-benzenedimethanamine;
N-(2-pyridinylmethyl)-N'-(6,7-dihydro-5H-cyclopenta[b]pyridin-7-yl)-1,4-benzenedimethanamine;
N-(2-pyridinylmethyl)-N'-(1,2,3,4-tetrahydro-1-naphthalenyl)-1,4-benzenedimethanamine;
N-(2-pyridinylmethyl)-N '-(1-naphthalenyl)-1,4-benzenedimethanamine;
N-(2-pyridinylmethyl)-N'-(8-quinolinyl)-1,4-benzenedimethanamine;
N-(2-pyridinylmethyl)-N'-[2-[(2-pyridinylmethyl)amino]ethyl]-N'-(1-methyl-1,2,3,4-tetrahydro-8-quinolinyl)-1,4-benzene dimethanamine;
N-(2-pyridinylmethyl)-N'-[2-[(1H-imidazol-2-ylmethyl)amino]ethyl]-N'-(1-methyl-1,2,3,4-tetrahydro-8-quinolinyl)-1,4-benzene dimethanamine;
N-(2-pyridinylmethyl)-N'-(1,2,3,4-tetrahydro-8-quinolinyl)-1,4-benzenedimethanamine;
N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine;
N-(2-pyridinylmethyl)-N'-(2-phenyl-5,6,7,8-tetrahydro-8-quinolinyl)-1,4-benzenedimethanamine;
N,N'-bis(2-pyridinylmethyl)-N'-(2-phenyl-5,6,7,8-tetrahydro-8-quinolinyl)-1,4-benzenedimethanamine;
N-(2-pyridinylmethyl)-N'-(5,6,7,8-tetrahydro-5-quinolinyl)-1,4-benzenedimethanamine;
N-(2-pyridinylmethyl)-N'-(1H-imidazol-2-ylmethyl)-N'-(5,6,7,8-tetrahydro-5-quinolinyl)-1,4-benzenedimethanamine;
N-(2-pyridinylmethyl)-N'-(1H-imidazol-2-ylmethyl)-N'-(5,6,7,8-tetrahydro-8-quinolinyl)-1,4-benzenedimethanamine;
N-(2-pyridinylmethyl)-N'-[(2-amino-3-phenyl)propyl]-N'-(5,6,7,8-tetrahydro-8-quinolinyl)-1,4-benzenedimethanamine;
N-(2-pyridinylmethyl)-N'-(1H-imidazol-4-ylmethyl)-N'-(5,6,7,8-tetrahydro-8-quinolinyl)-1,4-benzenedimethanamine;
N-(2-pyridinylmethyl)-N'-(2-quinolinylmethyl)-N'-(5,6,7,8-tetrahydro-8-quinolinyl)-1,4-benzenedimethanamine;

N-(2-pyridinylmethyl)-N'-(2-(2-naphthoyl)aminoethyl)-N'-(5,6,7,8-tetrahydro-8-quinolinyl)-1,4-benzenedimethanamine;

N-(2-pyridinylmethyl)-N'-[(S)-(2-acetylamino-3-phenyl)propyl]-N'-(5,6,7,8-tetrahydro-8-quinolinyl)-1,4-benzenedimethanamine;

N-(2-pyridinylmethyl)-N'-[(S)-(2-acetylamino-3-phenyl)propyl]-N'-(5,6,7,8-tetrahydro-8-quinolinyl)-1,4-benzenedimethanamine;

N-(2-pyridinylmethyl)-N'-[3-((2-naphthalenylmethyl)amino)propyl]-N'-(5,6,7,8-tetrahydro-8-quinolinyl)-1,4-benzenedimethanamine;

N-(2-pyridinylmethyl)-N'-[2-(S)-pyrollidinylmethyl]-N'-(5,6,7,8-tetrahydro-8-quinolinyl)-1,4-benzenedimethanamine;

N-(2-pyridinylmethyl)-N'-[2-(R)-pyrollidinylmethyl]-N'-(5,6,7,8-tetrahydro-8-quinolinyl)-1,4-benzenedimethanamine;

N-(2-pyridinylmethyl)-N'-[3-pyrazolylmethyl]-N'-(5,6,7,8-tetrahydro-8-quinolinyl)-1,4-benzenedimethanamine;

N-(2-pyridinylmethyl)-N'-[2-pyrrolylmethyl]-N'-(5,6,7,8-tetrahydro-8-quinolinyl)-1,4-benzenedimethanamine;

N-(2-pyridinylmethyl)-N'-[2-thiopheneylmethyl]-N'-(5,6,7,8-tetrahydro-8-quinolinyl)-1,4-benzenedimethanamine N-(2-pyridinylmethyl)-N'-[2-thiazolylmethyl]-N'-(5,6,7,8-tetrahydro-8-quinolinyl)-1,4-benzenedimethanamine;

N-(2-pyridinylmethyl)-N'-[2-furanylmethyl]-N'-(5,6,7,8-tetrahydro-8-quinolinyl)-1,4-benzenedimethanamine;

N-(2-pyridinylmethyl)-N'-[2-[(phenylmethyl)amino]ethyl]-N'-(5,6,7,8-tetrahydro-8-quinolinyl)-1,4-benzenedimethanamine;

N-(2-pyridinylmethyl)-N'-(2-aminoethyl)-N'-(5,6,7,8-tetrahydro-8-quinolinyl)-1,4-benzenedimethanamine;

N-(2-pyridinylmethyl)-N'-3-pyrrolidinyl-N'-(5,6,7,8-tetrahydro-8-quinolinyl)-1,4-benzenedimethanamine N-(2-pyridinylmethyl)-N'-4-piperidinyl-N'-(5,6,7,8-tetrahydro-8-quinolinyl)-1,4-benzenedimethanamine;

N-(2-pyridinylmethyl)-N'-[2-[(phenyl)amino]ethyl]-N'-(5,6,7,8-tetrahydro-8-quinolinyl)-1,4-benzenedimethanamine;

N-(2-pyridinylmethyl)-N'-(7-methoxy-1,2,3,4-tetrahydro-2-naphthalenyl)-1,4-benzenedimethanamine;

N-(2-pyridinylmethyl)-N'-(6-methoxy-1,2,3,4-tetrahydro-2-naphthalenyl)-1,4-benzenedimethanamine;

N-(2-pyridinylmethyl)-N'-(1-methyl-1,2,3,4-tetrahydro-2-naphthalenyl)-1,4-benzenedimethanamine;

N-(2-pyridinylmethyl)-N'-(7-methoxy-3,4-dihydronaphthalenyl)-1-(aminomethyl)-4-benzamide;

N-(2-pyridinylmethyl)-N'-(6-methoxy-3,4-dihydronaphthalenyl)-1-(aminomethyl)-4-benzamide;

N-(2-pyridinylmethyl)-N'-(1H-imidazol-2-ylmethyl)-N'-(7-methoxy-1,2,3,4-tetrahydro-2-naphthalenyl)-1,4-benzenedimethanamine;

N-(2-pyridinylmethyl)-N'-(8-hydroxy-1,2,3,4-tetrahydro-2-naphthalenyl)-1,4-benzenedimethanamine;

N-(2-pyridinylmethyl)-N'-(1H-imidazol-2-ylmethyl)-N'-(8-hydroxy-1,2,3,4-tetrahydro-2-naphthalenyl)-1,4-benzenedimethanamine;

N-(2-pyridinylmethyl)-N'-(8-Fluoro-1,2,3,4-tetrahydro-2-naphthalenyl)-1,4-benzenedimethanamine;

N-(2-pyridinylmethyl)-N'-(1H-imidazol-2-ylmethyl)-N'-(8-Fluoro-1,2,3,4-tetrahydro-2-naphthalenyl)-1,4-benzenedimethanamine;

N-(2-pyridinylmethyl)-N'-(5,6,7,8-tetrahydro-7-quinolinyl)-1,4-benzenedimethanamine;

N-(2-pyridinylmethyl)-N'-(1H-imidazol-2-ylmethyl)-N'-(5,6,7,8-tetrahydro-7-quinolinyl)-1,4-benzenedimethanamine;

N-(2-pyridinylmethyl)-N'-[2-[(2-naphthalenylmethyl)amino]ethyl]-N'-(5,6,7,8-tetrahydro-8-quinolinyl)-1,4-benzenedimethanamine;

N-(2-pyridinylmethyl)-N'-[2-(isobutylamino)ethyl]-N'-(5,6,7,8-tetrahydro-8-quinolinyl)-1,4-benzenedimethanamine;

N-(2-pyridinylmethyl)-N'-[2-[(2-pyridinylmethyl)amino]ethyl]-N'-(5,6,7,8-tetrahydro-8-quinolinyl)-1,4-benzenedimethanamine;

N-(2-pyridinylmethyl)-N'-[2-[(2-furanylmethyl)amino]ethyl]-N'-(5,6,7,8-tetrahydro-8-quinolinyl)-1,4-benzenedimethanamine;

N-(2-pyridinylmethyl)-N'-(2-guanidinoethyl)-N'-(5,6,7,8-tetrahydro-8-quinolinyl)-1,4-benzenedimethanamine;

N-(2-pyridinylmethyl)-N'-[2-[bis-[(2-methoxy)phenylmethyl]amino]ethyl]-N'-(5,6,7,8-tetrahydro-8-quinolinyl)-1,4-benzene dimethanamine;

N-(2-pyridinylmethyl)-N'-[2-[(1H-imidazol-4-ylmethyl)amino]ethyl]-N'-(5,6,7,8-tetrahydro-8-quinolinyl)-1,4-benzene dimethanamine;

N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine;

N-(2-pyridinylmethyl)-N'-[2-(phenylureido)ethyl]-N'-(5,6,7,8-tetrahydro-8-quinolinyl)-1,4-benzenedimethanamine;

N-(2-pyridinylmethyl)-N'-[[N''-(n-butyl)carboxamido]methyl]-N'-(5,6,7,8-tetrahydro-8-quinolinyl)-1,4-benzenedimethanamine;

N-(2-pyridinylmethyl)-N'-(carboxamidomethyl)-N'-(5,6,7,8-tetrahydro-8-quinolinyl)-1,4-benzenedimethanamine;

N-(2-pyridinylmethyl)-N'-[(N''-phenyl)carboxamidomethyl]-N'-(5,6,7,8-tetrahydro-8-quinolinyl)-1,4-benzenedimethanamine;

N-(2-pyridinylmethyl)-N'-(carboxymethyl)-N'-(5,6,7,8-tetrahydro-8-quinolinyl)-1,4-benzenedimethanamine;

N-(2-pyridinylmethyl)-N'-(phenylmethyl)-N'-(5,6,7,8-tetrahydro-8-quinolinyl)-1,4-benzenedimethanamine;

N-(2-pyridinylmethyl)-N'-(1H-benzimidazol-2-ylmethyl)-N'-(5,6,7,8-tetrahydro-8-quinolinyl)-1,4-benzenedimethanamine;

N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine (hydrobromide salt);

N-(2-pyridinylmethyl)-N'-(5-nitro-1H-benzimidazol-2-ylmethyl)-N'-(5,6,7,8-tetrahydro-8-quinolinyl)-1,4-benzenedimethanamine;

N-(2-pyridinylmethyl)-N'-[(1H)-5-azabenzimidazol-2-ylmethyl]-N'-(5,6,7,8-tetrahydro-8-quinolinyl)-1,4-benzenedimethanamine;

N-(2-pyridinylmethyl)-N-(4-phenyl-1H-imidazol-2-ylmethyl)-N'-(5,6,7,8-tetrahydro-8-quinolinyl)-1,4-benzenedimethanamine;

N-(2-pyridinylmethyl)-N'-[2-(2-pyridinyl)ethyl]-N'-(5,6,7,8-tetrahydro-8-quinolinyl)-1,4-benzenedimethanamine;

N-(2-pyridinylmethyl)-N'-(2-benzoxazolyl)-N'-(5,6,7,8-tetrahydro-8-quinolinyl)-1,4-benzenedimethanamine;

N-(2-pyridinylmethyl)-N'-(trans-2-aminocyclohexyl)-N'-(5,6,7,8-tetrahydro-8-quinolinyl)-1,4-benzenedimethanamine;

N-(2-pyridinylmethyl)-N'-(2-phenylethyl)-N'-(5,6,7,8-tetrahydro-8-quinolinyl)-1,4-benzenedimethanamine;

N-(2-pyridinylmethyl)-N'-(3-phenylpropyl)-N'-(5,6,7,8-tetrahydro-8-quinolinyl)-1,4-benzenedimethanamine;

N-(2-pyridinylmethyl)-N'-(trans-2-aninocyclopentyl)-N'-(5,6,7,8-tetrahydro-8-quinolinyl)-1,4-benzenedimethanamine;

N-[[4-[[(2-pyridinylmethyl)amino]methyl]phenyl]methyl]-N-(5,6,7,8-tetrahydro-8-quinolinyl)-glycinamide;

N-[[4-[[(2-pyridinylmethyl)amino]methyl]phenyl]methyl]-N-(5,6,7,8-tetrahydro-8-quinolinyl)-(L)-alaninamide;

N-[[4-[[(2-pyridinylmethyl)amino]methyl]phenyl]methyl]-N-(5,6,7,8-tetrahydro-8-quinolinyl)-(L)-aspartamide;

N-[[4-[[(2-pyridinylmethyl)amino]methyl]phenyl]methyl]-N-(5,6,7,8-tetrahydro-8-quinolinyl)-pyrazinamide;

N-[[4-[[(2-pyridinylmethyl)wnino]methyl]phenyl]methyl]-N-(5,6,7,8-tetrahydro-8-quinolinyl)-(L)-prolinamide;

N-[[4-[[(2-pyridinylmethyl)amino]methyl]phenyl]methyl]-N-(5,6,7,8-tetrahydro-8-quinolinyl)-(L)-lysinamide;

N-[[4-[[(2-pyridinylmethyl)amino]methyl]phenyl]methyl]-N-(5,6,7,8-tetrahydro-8-quinolinyl)-benzamide;

N-[[4-[[(2-pyridinylmethyl)amino]methyl]phenyl]methyl]-N-(5,6,7,8-tetrahydro-8-quinolinyl)-picolinamide;

N'-Benzyl-N-[[4-[[(2-pyridinylmethyl) amino]methyl]phenyl]methyl]-N-(5,6,7,8-tetrahydro-8-quinolinyl)-urea;

N'-phenyl-N-[[4-[[(2-pyridinylmethyl) amino]methyl]phenyl]methyl]-N-(5,6,7,8-tetrahydro-8-quinolinyl)-urea;

N-(6,7,8,9-tetrahydro-5H-cyclohepta[bacteriapyridin-9-yl)-4-[[(2-pyridinylmethyl)amino]methyl]benzamide;

N-(5,6,7,8-tetrahydro-8-quinolinyl)-4-[[(2-pyridinylmethyl)amino]methyl]benzamide;

N,N'-bis(2-pyridinylmethyl)-N'-(5,6,7,8-tetrahydro-8-quinolinyl)-1,4-benzenedimethanamine;

N,N'-bis(2-pyridinylmethyl)-N'-(6,7,8,9-tetrahydro-5H-cyclohepta[bacteriapyridin-9-yl)-1,4-benzenedimethanamine;

N,N'-bis(2-pyridinylmethyl)-N'-(6,7-dihydro-5H-cyclopenta[bacteriapyridin-7-yl)-1,4-benzenedimethanamine;

N,N'-bis(2-pyridinylmethyl)-N'-(1,2,3,4-tetrahydro-1-naphthalenyl)-1,4-benzenedimethanamine;

N,N'-bis(2-pyridinylmethyl)-N'-[(5,6,7,8-tetrahydro-8-quinolinyl)methyl]-1,4-benzenedimethanamine;

N,N'-bis(2-pyridinylmethyl)-N'[(6,7-dihydro-5H-cyclopenta[bacteriapyridin-7-yl)methyl]-1,4-benzenedimethanamine;

N-(2-pyridinylmethyl)-N-(2-methoxyethyl)-N'-(5,6,7,8-tetrahydro-8-quinolinyl)-1,4-benzenedimethanamine;

N-(2-pyridinylmethyl)-N-[2-(4-methoxyphenyl)ethyl]-N'-(5,6,7,8-tetrahydro-8-quinolinyl)-1,4-benzenedimethanamine;

N,N'-bis(2-pyridinylmethyl)-1,4-(5,6,7,8-tetrahydro-8-quinolinyl)benzenedimethanamine;

N-[(2,3-dimethoxyphenyl)methyl]-N'-(2-pyridinylmethyl)-N-(5,6,7,8-tetrahydro-8-quinolinyl)-1,4-benzenedimethanarnine;

N,N'-bis(2-pyridinylmethyl)-N-[1-(N"-phenyl-N"-methylureido)-4-piperidinyl]-1,3-benzenedimethanamine;

N,N'-bis(2-pyridinylmethyl)-N-[N"-p-toluenesulfonylphenylalanyl]-4-piperidinyl]-1,3-benzenedimethanamine;

N,N'-bis(2-pyridinylmethyl)-N-[1-[3-(2-chlorophenyl)-5-methyl-isoxazol-4-oyl]-4-piperidinyl]-1,3-benzenedimethanamine;

N-[(2-hydroxyphenyl)methyl]-N'-(2-pyridinylmethyl)-N-(6,7,8,9-tetrahydro-5H -cyclohepta[bacteriapyridin-9-yl)-1,4-benzenedimethanamine;

N-[(4-cyanophenyl)methyl]-N'-(2-pyridinylmethyl)-N-(6,7,8,9-tetrahydro-5H-cyclohepta[bacteriapyridin-9-yl)-1,4-benzenedimethanamine;

N-[(4-cyanophenyl)methyl]-N'-(2-pyridinylmethyl)-N-(5,6,7,8-tetrahydro-8-quinolinyl)-1,4-benzenedimethanamine;

N-[(4-acetamidophenyl)methyl]-N'-(2-pyridinylmethyl)-N-(5,6,7,8-tetrahydro-8-quinolinyl)-1,4-benzenedimethanamine;

N-[(4-phenoxyphenyl)methyl]-N'-(2-pyridinylmethyl)-N-(6,7,8,9-tetrahydro-5H-cyclohepta[bacteriapyridin-9-yl)-1,4-benzenedimethanamine;

N-[(1-methyl-2-carboxamido)ethyl]-N,N'-bis(2-pyridinylmethyl)-1,3-benzenedimethanamine;

N-[(4-benzyloxyphenyl)methyl]-N'-(2-pyridinylmethyl)-N-(6,7,8,9-tetrahydro-5H-cyclohepta[bacteriapyridin-9-yl)-1,4-benzenedimethanamine;

N-[(thiophene-2-yl)methyl]-N'-(2-pyridinylmethyl)-N-(6,7,8,9-tetrahydro-5H-cyclohepta[bacteriapyridin-9-yl)-1,4-benzenedimethanamine;

N-[1-(benzyl)-3-pyrrolidinyl]-N,N'-bis(2-pyridinylmethyl)-1,3-benzenedimethanamine;

N-[[1-methyl-3-(pyrazol-3-yl)]propyl]-N,N'-bis(2-pyridinylmethyl)-1,3-benzenedimethanamine;

N-[1-(phenyl)ethyl]-N,N'-bis(2-pyridinylmethyl)-1,3-benzenedimethanamine;

N-[(3,4-methylenedioxyphenyl)methyl]-N'-(2-pyridinylmethyl)-N-(6,7,8,9-tetrahydro-5H-cyclohepta[b]pyridin-9-yl)-1,4-benzenedimethanamine;

N-[1-benzyl-3-carboxymethyl-4-piperidinyl]-N,N'-bis(2-pyridinylmethyl)-1,3-benzenedimethanamine;

N-[(3,4-methylenedioxyphenyl)methyl]-N'-(2-pyridinylmethyl)-N-(5,6,7,8-tetrahydro-8-quinolinyl)-1,4-benzenedimethanamine;

N-(3-pyridinylmethyl)-N'-(2-pyridinylmethyl)-N-(6,7,8,9-tetrahydro-5H-cyclohepta[b]pyridin-9-yl)-1,4-benzenedimethanamine;

N-[[1-methyl-2-(2-tolyl)carboxamido]ethyl]-N,N'-bis(2-pyridinylmethyl)-1,3-benzenedimethanamine;

N-[(1,5-dimethyl-2-phenyl-3-pyrazolinone-4-yl)methyl]-N'-(2-pyridinylmethyl)-N -(5,6,7,8-tetrahydro-8-quinolinyl)-1,4-benzenedimethanamine;

N-[(4-propoxyphenyl)methyl]-N'-(2-pyridinylmethyl)-N-(6,7,8,9-tetrahydro-5H-cyclohepta[b]pyridin-9-yl)-1,4-benzenedimethanamine;

N-(1-phenyl-3,5-dimethylpyrazolin-4-ylmethyl)-N'-(2-pyridinylmethyl)-N-(5,6,7,8-tetrahydro-8-quinolinyl)-1,4-benzenedimethanamine;

N-[1H-imidazol-4-ylmethyl]-N,N'-bis(2-pyridinylmethyl)-1,3-benzenedimethanamine;

N-[(3-methoxy-4,5-methylenedioxyphenyl)methyl]-N'-(2-pyridinylmethyl)-N-(6,7,8,9-tetrahydro-5H-cyclohepta[b]pyridin-9-yl)-1,4-benzenedimethanamine;

N-[(3-cyanophenyl)methyl]-N'-(2-pyridinylmethyl)-N-(6,7,8,9-tetrahydro-5H-cyclohepta[b]pyridin-9-yl)-1,4-benzenedimethanamine;

N-[(3-cyanophenyl)methyl]-N'-(2-pyridinylmethyl)-N-(5,6,7,8-tetrahydro-8-quinolinyl)-1,4-benzenedimethanamine;

N-(5-ethylthiophene-2-ylmethyl)-N'-(2-pyridinylmethyl)-N-(6,7,8,9-tetrahydro-5H-cyclohepta[b]pyridin-9-yl)-1,4-benzenedimethanamine;

N-(5-ethylthiophene-2-ylmethyl)-N'-(2-pyridinylmethyl)-N-(5,6,7,8-tetrahydro-8-quinolinyl)-1,4-benzenedimethanamine;

N-[(2,6-difluorophenyl)methyl]-N'-(2-pyridinylmethyl)-N-(6,7,8,9-tetrahydro-5H-cyclohepta[b]pyridin-9-yl)-1,4-benzenedimethanamine;

N-[(2,6-difluorophenyl)methyl]-N'-(2-pyridinylmethyl)-N-(5,6,7,8-tetrahydro-8-quinolinyl)-1,4-benzenedimethanamine;

N-[(2-difluoromethoxyphenyl)methyl]-N'-(2-pyridinylmethyl)-N-(6,7,8,9-tetrahydro-5H-cyclohepta[b]pyridin-9-yl)-1,4-benzenedimethanamine;

N-(2-difluoromethoxyphenylmethyl)-N'-(2-pyridinylmethyl)-N-(5,6,7,8-tetrahydro-8-quinolinyl)-1,4-benzenedimethanamine;

N-(1,4-benzodioxan-6-ylmethyl)-N'-(2-pyridinylmethyl)-N-(6,7,8,9-tetrahydro-5H-cyclohepta[b]pyridin-9-yl)-1,4-benzenedimethanamine;

N,N'-bis(2-pyridinylmethyl)-N-[1-(N"-phenyl-N"-methylureido)-4-piperidinyl]-1,4-benzenedimethanamine;

N,N'-bis(2-pyridinylmethyl)-N-[N"-p-toluenesulfonylphenylalanyl]-4-piperidinyl]-1,4-benzenedimethanamine;

N-[1-(3-pyridinecarboxamido)-4-piperidinyl]-N,N'-bis(2-pyridinylmethyl)-1,4-benzenedimethanamine;

N-[1-(cyclopropylcarboxamido)-4-piperidinyl]-N,N'-bis(2-pyridinylmethyl)-1,4-benzenedimethanamine;

N-[1-(1-phenylcyclopropylcarboxamido)-4-piperidinyl]-N,N'-bis(2-pyridinylmethyl)-1,4-benzenedimethanamine;

N-(1,4-benzodioxan-6-ylmethyl)-N'-(2-pyridinylmethyl)-N-(5,6,7,8-tetrahydro-8-quinolinyl)-1,4-benzenedimethanamine;

N-[1 -[3-(2-chlorophenyl)-5-methyl-isoxazol-4-carboxamido]-4-piperidinyl]-N,N'-bis(2-pyridinylmethyl)-1,4-benzenedimethanamine;

N-[1-(2-thiomethylpyridine-3-carboxamido)-4-piperidinyl]-N,N'-bis(2-pyridinylmethyl)-1,4-benzenedimethanamine;

N-[(2,4-difluorophenyl)methyl]-N'-(2-pyridinylmethyl)-N-(5,6,7,8-tetrahydro-8-quinolinyl)-1,4-benzenedimethanamine;

N-(1-methylpyrrol-2-ylmethyl)-N'-(2-pyridinylmethyl)-N-(5,6,7,8-tetrahydro-8-quinolinyl)-1,4-benzenedimethanamine;

N-[(2-hydroxyphenyl)methyl]-N'-(2-pyridinylmethyl)-N-(5,6,7,8-tetrahydro-8-quinolinyl)-1,4-benzenedimethanamine;

N-[(3-methoxy-4,5-methylenedioxyphenyl)methyl]-N'-(2-pyridinylmethyl)-N-(5,6,7,8-tetrahydro-8-quinolinyl)-1,4-benzenedimethanamine;

N-(3-pyridinylmethyl)-N'-(2-pyridinylmethyl)-N-(5,6,7,8-tetrahydro-8-quinolinyl)-1,4-benzenedimethanamine;

N-[2-(N"-morpholinomethyl)-1-cyclopentyl]-N,N'-bis(2-pyridinylmethyl)-1,4-benzenedimethanamine;

N-[(1-methyl-3-piperidinyl)propyl]-N,N'-bis(2-pyridinylmethyl)-1,4-benzenedimethanamine;

N-(1-methylbenzimidazol-2-ylmethyl)-N'-(2-pyridinylmethyl)-N-(5,6,7,8-tetrahydro-8-quinolinyl)-1,4-benzenedimethanamine;

N-[1-(benzyl)-3-pyrrolidinyl]-N,N'-bis(2-pyridinylmethyl)-1,4-benzenedimethanamine;

N-[[(1-phenyl-3-(N"-morpholino)]propyl]-N,N'-bis(2-pyridinylmethyl)-1,4-benzenedimethanamine;

N-[1-(iso-propyl)-4-piperidinyl]-N,N'-bis(2-pyridinylmethyl)-1,4-benzenedimethanamine;

N-[1-(ethoxycarbonyl)-4-piperidinyl]-N'-(2-pyridinylmethyl)-N-(5,6,7,8-tetrahydro-8-quinolinyl)-1,4-benzenedimethanamine;

N-[(1-methyl-3-pyrazolyl)propyl]-N'-(2-pyridinylmethyl)-N-(5,6,7,8-tetrahydro-8-quinolinyl)-1,4-benzenedimethanamine;

N-[1-methyl-2-(N",N"-diethylcarboxamido)ethyl]-N,N'-bis(2-pyridinylmethyl)-1,4-benzenedimethanamine;

N-[(1-methyl-2-phenylsulfonyl)ethyl]-N'-(2-pyridinylmethyl)-N-(5,6,7,8-tetrahydro-8-quinolinyl)-1,4-benzenedimethanamine;

N-[(2-chloro-4,5-methylenedioxyphenyl)methyl]-N'-(2-pyridinylmethyl)-N-(5,6,7,8-tetrahydro-8-quinolinyl)-1,4-benzenedimethanamine;

N-[1-methyl-2-[N"-(4-chlorophenyl)carboxamido]ethyl]-N'-(2-pyridinylmethyl)-N-(5,6,7,8-tetrahydro-8-quinolinyl)-1,4-benzenedimethanamine;

N-(1-acetoxyindol-3-ylmethyl)-N'-(2-pyridinylmethyl)-N-(6,7,8,9-tetrahydro-5H-cyclohepta[b]pyridin-9-yl)-1,4-benzenedimethanamine;

N-[(3-benzyloxy-4-methoxyphenyl)methyl]-N'-(2-pyridinylmethyl)-N-(6,7,8,9-tetrahydro-5H-cyclohepta[b]pyridin-9-yl)-1,4-benzenedimethaniamine;

N-(3-quinolylmethyl)-N'-(2-pyridinylmethyl)-N-(5,6,7,8-tetrahydro-8-quinolinyl)-1,4-benzenedimethanamine;

N-[(8-hydroxy)-2-quinolylmethyl]-N'-(2-pyridinylmethyl)-N-(6,7,8,9-tetrahydro-5H-cyclohepta[b]pyridin-9-yl)-1,4-benzenedimethanamine;

N-(2-quinolylmethyl)-N'-(2-pyridinylmethyl)-N-(6,7,8,9-tetrahydro-5H-cyclohepta[b]pyridin-9-yl)-1,4-benzenedimethanamine;

N-[(4-acetamidophenyl)methyl]-N'-(2-pyridinylmethyl)-N-(6,7,8,9-tetrahydro-5H-cyclohepta[b]pyridin-9-yl)-1,4-benzenedimethanamine;

N-[1H-imidazol-2-ylmethyl]-N,N'-bis(2-pyridinylmethyl)-1,4-benzenedimethanamine;

N-(3-quinolylmethyl)-N'-(2-pyridinylmethyl)-N-(6,7,8,9-tetrahydro-5H-cyclohepta[b]pyridin-9-yl)-1,4-benzenedimethanamine;

N-(2-thiazolylmethyl)-N'-(2-pyridinylmethyl)-N-(6,7,8,9-tetrahydro-5H-cyclohepta[b]pyridin-9-yl)-1,4-benzenedimethanamine;

N-(4-pyridinylmethyl)-N'-(2-pyridinylmethyl)-N-(6,7,8,9-tetrahydro-5H-cyclohepta[b]pyridin-9-yl)-1,4-benzenedimethanamine;

N-[(5-benzyloxy)benzo[b]pyrrol-3-ylmethyl]-N,N'-bis(2-pyridinylmethyl)-1,4-benzenedimethanamine;

N-(1-methylpyrazol-2-ylmethyl)-N'-(2-pyridinylmethyl)-N-(6,7,8,9-tetrahydro-5H-cyclohepta[b]pyridin-9-yl)-1,4-benzenedimethanamine;

N-[(4-methyl)-1H-imidazol-5-ylmethyl]-N,N'-bis(2-pyridinylmethyl)-1,4-benzenedimethanamine;

N-[[(4-dimethylamino)-1-napthalenyl]methyl]-N,N'-bis(2-pyridinylmethyl)-1,4-benzenedimethanamine;

N-[1,5-dimethyl-2-phenyl-3-pyrazolinone-4-ylmethyl]-N,N'-bis(2-pyridinylmethyl)-1,4-benzenedimethanamine;

N-[1-[(1-acetyl-2-(R)-prolinyl]-4-piperidinyl]-N-[2-(2-pyridinyl)ethyl]-N'-(2-pyridinylmethyl)-1,3-benzenedimethanamine;

N-[1-[2-acetamidobenzoyl-4piperidinyl]-4-piperidinyl]-N-[2-(2-pyridinyl)ethyl]-N'-(2-pyridinylmethyl)-1,3-benzenedimethanamine;

N-[(2-cyano-2-phenyl)ethyl]-N'-(2-pyridinylmethyl)-N-(6,7,8,9-tetrahydro-5H-cyclohepta[b]pyridin-9-yl)-1,4-benzenedimethanamine;

N-[(N"'-acetyltryptophanyl)-4-piperidinyl]-N-[2-(2-pyridinyl)ethyl]-N'-(2-pyridinylmethyl)-1,3-benzenedimethanamine;

N-[(N"'-benzoylvalinyl)-4-piperidinyl]-N-[2-(2-pyridinyl)ethyl]-N'-(2-pyridinylmethyl)-1,3-benzenedimethanamine;

N-[(4-dimethylaminophenyl)methyl]-N'-(2-pyridinylmethyl)-N-(6,7,8,9-tetrahydro-5H-cyclohepta[b]pyridin-9-yl)-1,4-benzenedimethanamine;

N-(4-pyridinylmethyl)-N'-(2-pyridinylmethyl)-N-(5,6,7,8-tetrahydro-8-quinolinyl)-1,4-benzenedimethanamine;

N-(1-methylbenzimadazol-2-ylmethyl)-N'-(2-pyridinylmethyl)-N-(6,7,8,9-tetrahydro-5H-cyclohepta[b]pyridin-9-yl)-1,4-benzenedimethanamine;

N-[1-butyl-4-piperidinyl]-N-[2-(2-pyridinyl)ethyl]-N'-(2-pyridinylmethyl)-1,3-benzenedimethanamine;

N-[1-benzoyl-4-piperidinyl]-N-[2-(2-pyridinyl)ethyl]-N'-(2-pyridinylmethyl)-1,3-benzenedimethanamine;

N-[1-(benzyl)-3-pyrrolidinyl]-N-[2-(2-pyridinyl)ethyl]-N'-(2-pyridinylmethyl)-1,3-benzenedimethanamine;

N-[(1-methyl)benzo[b]pyrrol-3-ylmethyl]-N-[2-(2-pyridinyl)ethyl]-N'-(2-pyridinylmethyl)-1,3-benzenedimethanamine;

N-[1H-imidazol-4-ylmethyl]-N-[2-(2-pyridinyl)ethyl]-N'-(2-pyridinylmethyl)-1,3-benzenedimethanamine;

N-[1-(benzyl)-4-piperidinyl]-N-[2-(2-pyridinyl)ethyl]-N'-(2-pyridinylmethyl)-1,4-benzenedimethanamine;

N-[1-methylbenzimidazol-2-ylmethyl]-N-[2-(2-pyridinyl)ethyl]-N'-(2-pyridinylmethyl)-1,4-benzenedimethanamine;

N-[(2-phenyl)benzo[b]pyrrol-3-ylmethyl]-N-[2-(2-pyridinyl)ethyl]-N'-(2-pyridinylmethyl)-1,4-benzenedimethanamine;

N-[(6-methylpyridin-2-yl)methyl]-N'-(2-pyridinylmethyl)-N-(5,6,7,8-tetrahydro-8-quinolinyl)-1,4-benzenedimethanamine;

N-(3-methyl-1H-pyrazol-5-ylmethyl)-N'-(2-pyridinylmethyl)-N-(5,6,7,8-tetrahydro-8-quinolinyl)-1,3-benzenedimethanamine;

N-[(2-methoxyphenyl)methyl]-N'-(2-pyridinylmethyl)-N-(5,6,7,8-tetrahydro-8-quinolinyl)-1,3-benzenedimethanamine;

N-[(2-ethoxyphenyl)methyl]-N'-(2-pyridinylmethyl)-N-(6,7,8,9-tetrahydro-5H-cyclohepta[b]pyridin-9-yl)-1,3-benzenedimethanamine;

N-(benzyloxyethyl)-N'-(2-pyridinylmethyl)-N-(5,6,7,8-tetrahydro-8-quinolinyl)-1,3-benzenedimethanamine;

N-[(2-ethoxy-1-naphthalenyl)methyl]-N'-(2-pyridinylmethyl)-N-(5,6,7,8-tetrahydro-8-quinolinyl)-1,3-benzenedimethanamine;

N-[(6-methylpyridin-2-yl)methyl]-N'-(2-pyridinylmethyl)-N-(5,6,7,8-tetrahydro-8-quinolinyl)-1,3-benzenedimethanamine;

1-[[4-[[(2-pyridinylmethyl)amino]methyl]phenyl]methyl]guanidine;

N-(2-pyridinylmethyl)-N-(8-methyl-8-azabicyclo[3.2.1]octan-3-yl)-1,4-benzenedimethanamine;

1-[[4-[[(2-pyridinylmethyl)amino]methyl]phenyl]methyl]homopiperazine;

1-[[3-[[(2-pyridinylmethyl)amino]methyl]phenyl]methyl]homopiperazine;

trans and cis-1-[[4-[[(2-pyridinylmethyl)amino]methyl]phenyl]methyl]-3,5-piperidinediamine;

N,N'-[1,4-Phenylenebis(methylene)]bis-4-(2-pyrimidyl)piperazine;

1-[[4-[[(2-pyridinylmethyl)amino]methyl]phenyl]methyl]-1-(2-pyridinyl)methylamine;

2-(2-pyridinyl)-5-[[(2-pyridinylmethyl)amino]methyl]-1,2,3,4-tetrahydroisoquinoline;

1-[[4-[[(2-pyridinylmethyl)amino]methyl]phenyl]methyl]-3,4-diaminopyrrolidine;

1-[[4-[[(2-pyridinylmethyl)amino]methyl]phenyl]methyl]-3,4-diacetylaminopyrrolidine;

8-[[4-[[(2-pyridinylmethyl)amino]methyl]phenyl]methyl]-2,5,8-triaza-3-oxabicyclo[4.3.0]nonane;

8-[[4-[[(2-pyridinylmethyl)amino]methyl]phenyl]methyl]-2,5,8-triazabicyclo[4.3.0]nonane;

(4-Aminomethyl-pyridin-3-ylmethyl)-(1H-benzoimidazol-2-ylmethyl)-(5,6,7,8-tetrahydro-quinolin-8-yl)-amine;

(3-Aminomethyl-pyridin-4-ylmethyl)-(1H-benzoimidazol-2-ylmethyl)-(5,6,7,8-tetrahydro-quinolin-8-yl)-amine;

1-(3-Aminomethyl-4-{[(1H-benzoimidazol-2-ylmethyl)-(5,6,7,8-tetrahydro-quinolin-8-yl)-amino]-methyl}-phenyl)-ethanone;

1-(5-Aminomethyl-2-{[(1H-benzoimidazol-2-ylmethyl)-(5,6,7,8-tetrahydro-quinolin-8-yl)-amino]-methyl}-phenyl)-ethanone;

3-Aminomethyl-4-{[(1H-benzoimidazol-2-ylmethyl)-(5,6,7,8-tetrahydro-quinolin-8-yl)-amino]-methyl}-benzenesulfonamide;

5-Aminomethyl-2-{[(1H-benzoimidazol-2-ylmethyl)-(5,6,7,8-tetrahydro-quinolin-8-yl)-amino]-methyl}-benzenesulfonamide;

N-(3-Aminomethyl-4-{[(1H-benzoimidazol-2-ylmethyl)-(5,6,7,8-tetrahydro-quinolin-8-yl)-amino]-methyl}-benzyl)-hydroxylamine;

N-(5-Aminomethyl-2-{[(1H-benzoimidazol-2-ylmethyl)-(5,6,7,8-tetrahydro-quinolin-8-yl)-amino]-methyl}-benzyl)-hydroxylamine;

N-(3-Aminomethyl-4-{[(1H-benzoimidazol-2-ylmethyl)-(5,6,7,8-tetrahydro-quinolin-8-yl)-amino]-methyl}-benzyl)-O-methyl-hydroxylamine;

N-(5-Aminomethyl-2-{[(1H-benzoimidazol-2-ylmethyl)-(5,6,7,8-tetrahydro-quinolin-8-yl)-amino]-methyl}-benzyl)-O-methyl-hydroxylamine;

(4-Aminomethyl-2-methoxymethyl-benzyl)-(1H-benzoimidazol-2-ylmethyl)-(5,6,7,8-tetrahydro-quinolin-8-yl)-amine;

(2-Aminomethyl-4-methoxymethyl-benzyl)-(1H-benzoimidazol-2-ylmethyl)-(5,6,7,8-tetrahydro-quinolin-8-yl)-amine;

N-(2-{[(1H-Benzoimidazol-2-ylmethyl)-(5,6,7,8-tetrahydro-quinolin-8-yl)-amino]-methyl}-benzyl)-fonnamide;

N-(4-{[(1H-Benzoimidazol-2-ylmethyl)-(5,6,7,8-tetrahydro-quinolin-8-yl)-amino]-methyl}-benzyl)-formamide;

N-(2-{[(1H-Benzoimidazol-2-ylmethyl)-(5,6,7,8-tetrahydro-quinolin-8-yl)-amino]-methyl}-benzyl)-hydroxylamine;

(1H-Benzoimidazol-2-ylmethyl)-(2,6-bis-aminomethyl-benzyl)-(5,6,7,8-tetrahydro-quinolin-8-yl)-amine;

(3-Aminomethyl-2-{[(1H-benzoimidazol-2-ylmethyl)-(5,6,7,8-tetrahydro-quinolin-8-yl)-amino]-methyl}-phenyl)-methanol;

(2-Aminomethyl-6-methoxymethyl-benzyl)-(1H-benzoimidazol-2-ylmethyl)-(5,6,7,8-tetrahydro-quinolin-8-yl)-amine;

N-(3-Aminomethyl-2-{[(1H-benzoimidazol-2-ylmethyl)-(5,6,7,8-tetrahydro-quinolin-8-yl)-amino]-methyl}-benzyl)-hydroxylamine;

N-(3-Aminomethyl-2-{[(1H-benzoimidazol-2-ylmethyl)-(5,6,7,8-tetrahydro-quinolin-8-yl)-amino]-methyl}-benzyl)-O-methyl-hydroxylamine;

[2-Aminomethyl-4-(1H-imidazol-2-yl)-benzyl]-(1H-benzoimidazol-2-ylmethyl)-(5,6,7,8-tetrahydro-quinolin-8-yl)-amine;

[2-Aminomethyl-4-(1-methyl-1H-imidazol-2-yl)-benzyl]-(1H-benzoimidazol-2-ylmethyl)-(5,6,7,8-tetrahydro-quinolin-8-yl)-amine;

[2-Aminomethyl-4-(2H-pyrazol-3-yl)-benzyl]-(1H-benzoimidazol-2-ylmethyl)-(5,6,7,8-tetrahydro-quinolin-8-yl)-amine;

[2-Aminomethyl-4-(1-methyl-1H-pyrazol-3-yl)-benzyl]-(1H-benzoimidazol-2-ylmethyl)-(5,6,7,8-tetrahydro-quinolin-8-yl)-amine;

[2-Aminomethyl-4-(1H-[1,2,4]triazol-3-yl)-benzyl]-(1H-benzoimidazol-2-ylmethyl)-(5,6,7,8-tetrahydro-quinolin-8-yl)-amine;

[2-Aminomethyl-4-(1-methyl-1H-[1,2,4]triazol-3-yl)-benzyl]-(1H-benzoimidazol-2-ylmethyl)-(5,6,7,8-tetrahydro-quinolin-8-yl)-amine;

(2-Aminomethyl-4-oxazol-2-yl-benzyl)-(1H-benzoimidazol-2-ylmethyl)-(5,6,7,8-tetrahydro-quinolin-8-yl)-amine;

(2-Aminomethyl-4-furan-2-yl-benzyl)-(1H-benzoimidazol-2-ylmethyl)-(5,6,7,8-tetrahydro-quinolin-8-yl)-amine;

[2-Aminomethyl-4-(tetrahydro-furan-2-yl)-benzyl]-(1H-benzoimidazol-2-ylmethyl)-(5,6,7,8-tetrahydro-quinolin-8-yl)-amine;

(2-Aminomethyl-4-thiazol-2-yl-benzyl)-(1H-benzoimidazol-2-ylmethyl)-(5,6,7,8-tetrahydro-quinolin-8-yl)-amine;

[2-Aminomethyl-4-(1H-tetrazol-5-yl)-benzyl]-(1H-benzoimidazol-2-ylmethyl)-(5,6,7,8-tetrahydro-quinolin-8-yl)-amine;

[2-Aminomethyl-4-(2-methyl-2H-tetrazol-5-yl)-benzyl]-(1H-benzoimidazol-2-ylmethyl)-(5,6,7,8-tetrahydro-quinolin-8-yl)-amine;

(2-Aminomethyl-4-pyridin-2-yl-benzyl)-(1H-benzoimidazol-2-ylmethyl)-(5,6,7,8-tetrahydro-quinolin-8-yl)-amine;

(2-Aminomethyl-4-piperidin-2-yl-benzyl)-(1H-benzoimidazol-2-ylmethyl)-(5,6,7,8-tetrahydro-quinolin-8-yl)-amine;

(4-Aminomethyl-3-{[(1H-benzoimidazol-2-ylmethyl)-(5,6,7,8-tetrahydro-quinolin-8-yl)-amino]-methyl}-phenyl)-methanol;

(2-Aminomethyl-5-methoxymethyl-benzyl)-(1H-benzoimidazol-2-ylmethyl)-(5,6,7,8-tetrahydro-quinolin-8-yl)-amine;

(4-Aminomethyl-5-{[(1H-benzoimidazol-2-ylmethyl)-(5,6,7,8-tetrahydro-quinolin-8-yl)-amino]-methyl}-pyridin-2-yl)-methanol;

(4-Aminomethyl-6-methoxymethyl-pyridin-3-ylmethyl)-(1H-benzoimidazol-2-ylmethyl)-(5,6,7,8-tetrahydro-quinolin-8-yl)-amine;

(1H-Benzoimidazol-2-ylmethyl)-(4,6-bis-aminomethyl-pyridin-3-ylmethyl)-(5,6,7,8-tetrahydro-quinolin-8-yl)-amine;

(4-Allylaminomethyl-2-aminomethyl-benzyl)-(1H-benzoimidazol-2-ylmethyl)-(5,6,7,8-tetrahydro-quinolin-8-yl)-amine;

(2-Allylaminomethyl-4-aminomethyl-benzyl)-(1H-benzoimidazol-2-ylmethyl)-(5,6,7,8-tetrahydro-quinolin-8-yl)-amine;

(2-Aminomethyl-4-cyclopropylaminomethyl-benzyl)-(1H-benzoimidazol-2-ylmethyl)-(5,6,7,8-tetrahydro-quinolin-8-yl)-amine;

(4-Aminomethyl-2-cyclopropylaminomethyl-benzyl)-(1H-benzoimidazol-2-ylmethyl)-(5,6,7,8-tetrahydro-quinolin-8-yl)-amine;

(2-Aminomethyl-5-chloro-benzyl)-(1H-benzoimidazol-2-ylmethyl)-(5,6,7,8-tetrahydro-quinolin-8-yl)-amine;

(2-Aminomethyl-5-bromo-benzyl)-(1H-benzoimidazol-2-ylmethyl)-(5,6,7,8-tetrahydro-quinolin-8-yl)-amine;

(2-Aminomethyl-5-nitro-benzyl)-(1H-benzoimidazol-2-ylmethyl)-(5,6,7,8-tetrahydro-quinolin-8-yl)-amine;

4-Aminomethyl-3-{[(1H-benzoimidazol-2-ylmethyl)-(5,6,7,8-tetrahydro-quinolin-8-yl)-amino]-methyl}-benzonitrile;

(5-Amino-2-aminomethyl-benzyl)-(1H-benzoimidazol-2-ylmethyl)-(5,6,7,8-tetrahydro-quinolin-8-yl)-amine;

(2-Aminomethyl-5-trifluoromethyl-benzyl)-(1H-benzoimidazol-2-ylmethyl)-(5,6,7,8-tetrahydro-quinolin-8-yl)-amine;

(2-Aminomethyl-4-fluoro-benzyl)-(1H-benzoimidazol-2-ylmethyl)-(5,6,7,8-tetrahydro-quinolin-8-yl)-amine;

(2-Aminomethyl-4-chloro-benzyl)-(1H-benzoimidazol-2-ylmethyl)-(5,6,7,8-tetrahydro-quinolin-8-yl)-amine;

(2-Aminomethyl-4-bromo-benzyl)-(1H-benzoimidazol-2-ylmethyl)-(5,6,7,8-tetrahydro-quinolin-8-yl)-amine;
(2-Aminomethyl-4-nitro-benzyl)-(1H-benzoimidazol-2-ylmethyl)-(5,6,7,8-tetrahydro-quinolin-8-yl)-amine;
3-Aminomethyl-4-{[(1H-benzoimidazol-2-ylmethyl)-(5,6,7,8-tetrahydro-quinolin-8-yl)-amino]-methyl}-benzonitrile;
(4-Amino-2-aminomethyl-benzyl)-(1H-benzoimidazol-2-ylmethyl)-(5,6,7,8-tetrahydro-quinolin-8-yl)-amine;
(2-Aminomethyl-4-trifluoromethyl-benzyl)-(1H-benzoimidazol-2-ylmethyl)-(5,6,7,8-tetrahydro-quinolin-8-yl)-amine;
(4-Aminomethyl-2-fluoro-benzyl)-(1H-benzoimidazol-2-ylmethyl)-(5,6,7,8-tetrahydro-quinolin-8-yl)-amine;
(4-Aminomethyl-2-chloro-benzyl)-(1H-benzoimidazol-2-ylmethyl)-(5,6,7,8-tetrahydro-quinolin-8-yl)-amine
(4-Aminomethyl-2-bromo-benzyl)-(1H-benzoimidazol-2-ylmethyl)-(5,6,7,8-tetrahydro-quinolin-8-yl)-amine;
(4-Aminomethyl-2-nitro-benzyl)-(1H-benzoimidazol-2-ylmethyl)-(5,6,7,8-tetrahydro-quinolin-8-yl)-amine;
5-Aminomethyl-2-{[(1H-benzoimidazol-2-ylmethyl)-(5,6,7,8-tetrahydro-quinolin-8-yl)-amino]-methyl}-benzonitrile;
(2-Amino-4-aminomethyl-benzyl)-(1H-benzoimidazol-2-ylmethyl)-(5,6,7,8-tetrahydro-quinolin-8-yl)-amine;
(4-Aminomethyl-2-trifluoromethyl-benzyl)-(1H-benzoimidazol-2-ylmethyl)-(5,6,7,8-tetrahydro-quinolin-8-yl)-amine;
(5-Aminomethyl-thiophen-2-ylmethyl)-(1H-benzoimidazol-2-ylmethyl)-(5,6,7,8-tetrahydro-quinolin-8-yl)-amine;
(4-Aminomethyl-thiophen-3-ylmethyl)-(1H-benzoimidazol-2-ylmethyl)-(5,6,7,8-tetrahydro-quinolin-8-yl)-amine;
(4-Aminomethyl-furan-3-ylmethyl)-(1H-benzoimidazol-2-ylmethyl)-(5,6,7,8-tetrahydro-quinolin-8-yl)-amine
(4-Aminomethyl-1H-pyrrol-3-ylmethyl)-(1H-benzoimidazol-2-ylmethyl)-(5,6,7,8-tetrahydro-quinolin-8-yl)-amine;
(4-Aminomethyl-1-methyl-1H-pyrrol-3-ylmethyl)-(1H-benzoimidazol-2-ylmethyl)-(5,6,7,8-tetrahydro-quinolin-8-yl)-amine;
(4-Aminomethyl-1H-pyrazol-3-ylmethyl)-(1H-benzoimidazol-2-ylmethyl)-(5,6,7,8-tetrahydro-quinolin-8-yl)-amine;
(4-Aminomethyl-1-methyl-1H-pyrazol-3-ylmethyl)-(1H-benzoimidazol-2-ylmethyl)-(5,6,7,8-tetrahydro-quinolin-8-yl)-amine;
(3-Aminomethyl-1H-pyrazol-4-ylmethyl)-(1H-benzoimidazol-2-ylmethyl)-(5,6,7,8-tetrahydro-quinolin-8-yl)-amine;
(3-Aminomethyl-1-methyl-1H-pyrazol-4-ylmethyl)-(1H-benzoimidazol-2-ylmethyl)-(5,6,7,8-tetrahydro-quinolin-8-yl)-amine;
(5-Aminomethyl-3H-imidazol-4-ylmethyl)-(1H-benzoimidazol-2-ylmethyl)-(5,6,7,8-tetrahydro-quinolin-8-yl)-amine;
(5-Aminomethyl-1-methyl-1H-imidazol-4-ylmethyl)-(1H-benzoimidazol-2-ylmethyl)-(5,6,7,8-tetrahydro-quinolin-8-yl)-amine;
(5-Aminomethyl-thiazol-4-ylmethyl)-(1H-benzoimidazol-2-ylmethyl)-(5,6,7,8-tetrahydro-quinolin-8-yl)-amine;
(5-Aminomethyl-pyrimidin-4-ylmethyl)-(1H-benzoimidazol-2-ylmethyl)-(5,6,7,8-tetrahydro-quinolin-8-yl)-amine;
(5-Aminomethyl-pyridazin-4-ylmethyl)-(1H-benzoimidazol-2-ylmethyl)-(5,6,7,8-tetrahydro-quinolin-8-yl)-amine;
(5-Allylaminomethyl-2-{[(1H-benzoimidazol-2-ylmethyl)-(5,6,7,8-tetrahydro-quinolin-8-yl)-amino]-methyl}-phenyl)-methanol;
(3-Allylaminomethyl-4-{[(1H-benzoimidazol-2-ylmethyl)-(5,6,7,8-tetrahydro-quinolin-8-yl)-amino]-methyl}-phenyl)-methanol;
(4-Allylaminomethyl-2-methoxymethyl-benzyl)-(1H-benzoimidazol-2-ylmethyl)-(5,6,7,8-tetrahydro-quinolin-8-yl)-amine;
(3-Allylaminomethyl-4-methoxymethyl-benzyl)-(1H-benzoimidazol-2-ylmethyl)-(5,6,7,8-tetrahydro-quinolin-8-yl)-amine;
(2-{[(1H-Benzoimidazol-2-ylmethyl)-(5,6,7,8-tetrahydro-quinolin-8-yl)-amino]-methyl}-5-cyclopropylaminomethyl-phenyl)-methanol;
(4-{[(1H-Benzoimidazol-2-ylmethyl)-(5,6,7,8-tetrahydro-quinolin-8-yl)-amino]-methyl}-3-cyclopropylaminomethyl-phenyl)-methanol;
(1H-Benzoimidazol-2-ylmethyl)-(4-cyclopropylaminomethyl-2-methoxymethyl-benzyl)-(5,6,7,8-tetrahydro-quinolin-8-yl)-amine;
(1H-Benzoimidazol-2-ylmethyl)-(2-cyclopropylaminomethyl-4-methoxymethyl-benzyl)-(5,6,7,8-tetrahydro-quinolin-8-yl)-amine;
5-Aminomethyl-2-{[(1H-benzoimidazol-2-ylmethyl)-(5,6,7,8-tetrahydro-quinolin-8-yl)-amino]-methyl}-benzamide;
5-Aminomethyl-2-{[(1H-benzoimidazol-2-ylmethyl)-(5,6,7,8-tetrahydro-quinolin-8-yl)-amino]-methyl}-N-hydroxy-benzamide;
5-Aminomethyl-2-{[(1H-benzoimidazol-2-ylmethyl)-(5,6,7,8-tetrahydro-quinolin-8-yl)-amino]-methyl}-benzoic acid hydrazide;
5-Aminomethyl-2-{[(1H-benzoimidazol-2-ylmethyl)-(5,6,7,8-tetrahydro-quinolin-8-yl)-amino]-methyl}-benzoic acid;
(1H-Benzoimidazol-2-ylmethyl)-(2,4-bis-allylaminomethyl-benzyl)-(5,6,7,8-tetrahydro-quinolin-8-yl)-amine;
(4-Allylaminomethyl-2-cyclopropylaminomethyl-benzyl)-(1H-benzoimidazol-2-ylmethyl)-(5,6,7,8-tetrahydro-quinolin-8-yl)-amine;
(2-Allylaminomethyl-4-cyclopropylaminomethyl-benzyl)-(1H-benzoimidazol-2-ylmethyl)-(5,6,7,8-tetrahydro-quinolin-8-yl)-amine;
(1H-Benzoimidazol-2-ylmethyl)-(2,4-bis-cyclopropylaminomethyl-benzyl)-(5,6,7,8-tetrahydro-quinolin-8-yl)-amine;
(2-Aminomethyl-4-propyl-benzyl)-(1H-benzoimidazol-2-ylmethyl)-(5,6,7,8-tetrahydro-quinolin-8-yl)-amine;
(4-Allyl-2-aminomethyl-benzyl)-(1H-benzoimidazol-2-ylmethyl)-(5,6,7,8-tetrahydro-quinolin-8-yl)-amine;
Acetic acid 3-aminomethyl-4-{[(1H-benzoimidazol-2-ylmethyl)-(5,6,7,8-tetrahydro-quinolin-8-yl)-amino]-methyl}-benzyl ester;
Acetic acid 5-aminomethyl-2-{[(1H-benzoimidazol-2-ylmethyl)-(5,6,7,8-tetrahydro-quinolin-8-yl)-amino]-methyl}-benzyl ester;
Acetic acid 4-{[(1H-benzoimidazol-2-ylmethyl)-(5,6,7,8-tetrahydro-quinolin-8-yl)-amino]-methyl}-3-cyclopropylaminomethyl-benzyl ester;
Acetic acid 2-{[(1H-benzoimidazol-2-ylmethyl)-(5,6,7,8-tetrahydro-quinolin-8-yl)-amino]-methyl}-5-cyclopropylaminomethyl-benzyl ester;

Acetic acid 3-allylaminomethyl-4-{[(1H-benzoimidazol-2-ylmethyl)-(5,6,7,8-tetrahydro-quinolin-8-yl)-amino]-methyl}-benzyl ester;
Acetic acid 5-allylaminomethyl-2-{[(1H-benzoimidazol-2-ylmethyl)-(5,6,7,8-tetrahydro-quinolin-8-yl)-amino]-methyl}-benzyl ester;
5-Aminomethyl-2-{[(1H-benzoimidazol-2-ylmethyl)-(5,6,7,8-tetrahydro-quinolin-8-yl)-amino]-methyl}-benzaldehyde oxime;
3-Aminomethyl-4-{[(1H-benzoimidazol-2-ylmethyl)-(5,6,7,8-tetrahydro-quinolin-8-yl)-amino]-methyl}-benzaldehyde oxime;
N-(5-Aminomethyl-2-{[(1H-benzoimidazol-2-ylmethyl)-(5,6,7,8-tetrahydro-quinolin-8-yl)-amino]-methyl}-benzyl)-acetamide;
N-(3-Aminomethyl-4-{[(1H-benzoimidazol-2-ylmethyl)-(5,6,7,8-tetrahydro-quinolin-8-yl)-amino]-methyl}-benzyl)-acetamide;
N-(3-(Acetylamino-methyl)-4-{[(1H-benzoimidazol-2-ylmethyl)-(5,6,7,8-tetrahydro-quinolin-8-yl)-amino]-methyl}-benzyl)-acetamide;
N-(2-{[(1H-Benzoimidazol-2-ylmethyl)-(5,6,7,8-tetrahydro-quinolin-8-yl)-amino]-methyl}-benzyl)-acetamide;
(6-Amninomethyl-1,3-dihydro-isobenzofuran-5-ylmethyl)-(1H-benzoimidazol-2-ylmethyl)-(5,6,7,8-tetrahydro-quinolin-8-yl)-amine;
(4-Aminomethyl-1,3-dihydro-isobenzofuran-5-ylmethyl)-(1H-benzoimidazol-2-ylmethyl)-(5,6,7,8-tetrahydro-quinolin-8-yl)-amine;
(7-Aminomethyl-1,3-dihydro-isobenzofuran-4-ylmethyl)-(1H-benzoimidazol-2-ylmethyl)-(5,6,7,8-tetrahydro-quinolin-8-yl)-amine;
N'-(1H-benzimidazol-2-ylmethyl)-N'-(5,6,7,8-tetrahydro-8-quinolinyl)-1,3-benzenedimethanamine;
(1H-Benzimidazol-2-ylmethyl)-(2-Aminomethyl-benzyl)-(5,6,7,8-tetrahydro-quinolin-8-yl)-amine (hydrobromide salt);
(2-Aminomethyl-benzyl)-(1H-benzimidazol-2-ylmethyl)-(S)-5,6,7,8-tetrahydro-quinolin-8-yl-amine (hydrochloride salt);
(3-aminomethyl-4-{[(1H-benzoimidazol-2-ylmethyl)-(5,6,7,8-tetrahydro-quinolin-8-yl)-amino]-methyl}-phenyl)-methanol;
(2-Aminomethyl-3-methoxy-benzyl)-(1H-benzimidazol-2-ylmethyl)-(5,6,7,8-tetrahydro-quinolin-8-yl)-amine (hydrobromide salt);
(1H-Benzimidazol-2-ylmethyl)-(5,6,7,8-tetrahydroquinolin-8-yl)-[(1-aminomethyl)-benzoxazol-3-ylmethyl)]-amine (hydrobromide salt);
(1H-Benzimidazol-2-ylmethyl)-(5,6,7,8-tetrahydroquinolin-8-yl)-[(1-benzyl-2-aminomethyl)-imidazol-5-ylmethyl)]-amine;
6-aminomethylpyridin-3-ylmethyl-(1H-benzimidazol-2-ylmethyl)-(5,6,7,8-tetrahydroquinolin-8-yl)-amine;
[4-(2-amino-ethyl)-benzyl]-(1H-benzoimidazol-2-ylmethyl)-(5,6,7,8-tetrahydro-quinolin-8-yl)-amine (hydrobromide salt);
[4-(3-amino-propyl)-benzyl]-(1H-benzoimidazol-2-ylmethyl)-(5,6,7,8-tetrahydro-quinolin-8-yl)-amine (hydrobromide salt);
N-(4-{[(1H-benzimidazol-2-ylmethyl)-(5,6,7,8-tetrahydro-quinolin-8-yl)-amino]-methyl}-benzyl)-hydroxylamine;
(5-aminomethyl-2-{[(1H-benzoimidazol-2-ylmethyl)-(5,6,7,8-tetrahydro-quinolin-8-yl)-amino]-methyl}-phenyl)-methanol;
2-Aminomethyl-5-{[(1H-benzimidazol-2-ylmethyl)-(5,6,7,8-tetrahydro-quinolin-8-yl)-amino]-methyl}-phenol (hydrobromide salt);
(4-Aminomethyl-3-methoxy-benzyl)-(1H-benzimidazol-2-ylmethyl)-(5,6,7,8-tetrahydro-quinolin-8-yl)-amine (hydrobromide salt);
(1H-benzoimidazol-2-ylmethyl)-(2,4-bis-aminomethyl-benzyl)-(5,6,7,8-tetrahydro-quinolin-8-yl)-amine (hydrobromide salt);
5-Aminomethyl-2-{[(1H-benzoimidazol-2-ylmethyl)-(5,6,7,8-tetrahydro-quinolin-8-yl)-amino]-methyl}-benzoic acid methyl ester (hydrobromide salt);
3-aminomethyl-4-{[(1H-benzimidazole-2-ylmethyl)-(5,6,7,8-tetrahydro-quinolin-8-yl)-amino]-methyl}-benzoic acid hydrobromide salt;
3-aminomethyl-4-{[(1H-benzimidazole-2-ylmethyl)-(5,6,7,8-tetrahydro-quinolin-8-yl)-amino]-methyl}-N-hydroxy-benzamide hydrobromide salt;
3-aminomethyl-4-{[(1H-benzimidazole-2-ylmethyl)-(5,6,7,8-tetrahydro-quinolin-8-yl)-amino]-methyl}-benzamide hydrobromide salt;
3-Aminomethyl-4-{[(1H-benzimidazole-2-ylmethyl)-(5,6,7,8-tetrahydro-quinolin-8-yl)-amino]-methyl}-benzoic acid hydrazide (hydrobromide salt);
(2-aminomethyl-5-fluorobenzyl)-(1H-benzimidazol-2-ylmethyl)-(5,6,7,8-tetrahydro-quinolin-8-yl)-amine (hydrobromide salt);
3-aminomethyl-4-{[(1H-benzimidazol-2-ylmethyl)-(5,6,7,8-tetrahydro-quinolin-8-yl)-amino]-methyl}-benzoic acid methyl ester;
(2-aminomethyl-4-methoxymethyl-benzyl)-(1H-benzimidazol-2-ylmethyl)-(5,6,7,8-tetrahydro-quinolin-8-yl)-amine;
N-(2-{[(1H-benzimidazol-2-ylmethyl)-(5,6,7,8-tetrahydroquinolin-8-yl)-amino]-methyl}-benzyl)-guanidine;
N-(4-{[(1H-benzimidazol-2-ylmethyl)-(5,6,7,8-tetrahydroquinolin-8-yl)-amino]-methyl}-benzyl)-guanidine (hydrobromide salt);
N'-(4-{[(1H-Benzimidazol-2-ylmethyl)-(5,6,7,8-tetrahydro-quinolin-8-yl)-amino]-methyl}-benzyl)-N,N-dimethyl-guanidine (hydrobromide salt);
[4-(1H-benzimidazol-2-ylmethyl)-(5,6,7,8-tetrahydro-quinolin-8-yl)-aminomethylbenzyl]-N,N-dimethylformamidine (hydrobromide salt);
N-(4-{[(1H-Benzimidazol-2-ylmethyl)-(5,6,7,8-tetrahydro-quinolin-8-yl)-amino]-methyl}-benzyl)-benzamidine (hydrobromide salt);
N-(4-{[(1H-Benzimidazol-2-ylmethyl)-(5,6,7,8-tetrahydro-quinolin-8-yl)-amino]-methyl}-benzyl)-acetamidine (hydrobromide salt);
N-isobutyl-N'-(1H-benzimidazol-2-ylmethyl)-N'-(5,6,7,8-tetrahydro-8-quinolinyl)-1,4-benzenedimethanamine (hydrobromide salt);
(1H-Benzimidazol-2-ylmethyl)-(4-piperidin-2-yl-benzyl)-(5,6,7,8-tetrahydro-quinolin-8-yl)-amine (hydrobromide salt);
(1H-Benzimidazol-2-ylmethyl)-(4-piperidin-1-ylmethyl-benzyl)-(5,6,7,8-tetrahydro-quinolin-8-yl)-amine (hydrobromide salt);
(1H-Benzimidazol-2-ylmethyl)-(4-methylaminomethyl-benzyl)-(5,6,7,8-tetrahydro-quinolin-8-yl)-amine (hydrobromide salt);
(1H-Benzimidazol-2-ylmethyl)-(4-piperazin-1-ylmethyl-benzyl)-(5,6,7,8-tetrahydro-quinolin-8-yl)-amine (hydrobromide salt);

[4-(4-Allyl-piperazin-1-ylmethyl)-benzyl]-(1H-benzimidazol-2-ylmethyl)-(5,6,7,8-tetrahydro-quinolin-8-yl)-amine (hydrobromide salt);

(1H-Benzimidazol-2-ylmethyl)-(4-dimethylaminomethyl-benzyl)-(5,6,7,8-tetrahydro-quinolin-8-yl)-amine (hydrobromide salt);

(1H-Benzimidazol-2-ylmethyl)-(5,6,7,8-tetrahydro-quinolin-8-yl)-[4-(1,2,4-triazol-4-yliminomethyl)-benzyl]-amine (hydrobromide salt);

N'-(4-{[(1H-Benzimidazol-2-ylmethyl)-(5,6,7,8-tetrahydro-quinolin-8-yl)-amino]-methyl}-benzyl)-ethane-1,2-diamine (hydrobromide salt);

(1H-benzimidazol-2-ylmethyl)-(4-butylaminomethyl-benzyl)-(5,6,7,8-tetrahydro-quinolin-8-yl)-amine;

(1H-benzimidazol-2-ylmethyl)-(4-diallylaminomethyl-benzyl)-(5,6,7,8-tetrahydro-quinolin-8-yl)-amine;

(4-allylaminomethyl-benzyl)-(1H-benzimidazol-2-ylmethyl)-(5,6,7,8-tetrahydro-quinolin-8-yl)-amine;

(1H-benzimidazol-2-ylmethyl)-(4-pyrrolidin-1-ylmethyl-benzyl)-(5,6,7,8-tetrahydro-quinolin-8-yl)-amine;

(1H-Benzimidazol-2-ylmethyl)-(4-morpholin-4-ylmethyl-benzyl)-(5,6,7,8-tetrahydro-quinolin-8-yl)-amine (hydrobromide salt);

(1H-benzoimidazol-2-ylmethyl)-(5,6,7,8-tetrahydro-quinolin-8-yl)-(4-thiomorpholin-4-ylmethyl-benzyl)-amine;

(1H-Benzimidazol-2-ylmethyl)-(5,6,7,8-tetrahydro-quinolin-8-yl)-(2-cyclopropylaminomethyl-benzyl)-amine (HBr salt);

(1H-Benzimidazol-2-ylmethyl)-(5,6,7,8-tetrahydro-quinolin-8-yl)-(2-allylaminomethyl -benzyl)-amine (HBr salt);

(1H-Benzimidazol-2-ylmethyl)-[2-(R)-(2-aminopropionamidylmethyl)-benzyl]-(5,6,7,8-tetrahydro-quinolin-8-yl)-amine (hydrobromide salt);

(1H-benzimidazol-2-ylmethyl)-[2-(1H-benzimidazol-2-ylmethyl)-aminobenzyl]-(5,6,7,8-tetrahydroquinolin-8-yl)-amine;

(2-aminobenzyl)-(1H-benzimidazol-2-ylmethyl)-(5,6,7,8-tetrahydroquinolin-8-yl)-amine;

(1H-Benzimidazol-2-ylmethyl)-(2-cyano-benzyl)-(5,6,7,8-tetrahydro-quinolin-8-yl)-amine (hydrobromide salt);

2-{[(1H-Benzimidazol-2-ylmethyl)-(5,6,7,8-tetrahydro-quinolin-8-yl)-amino]-methyl}-6-methoxy-benzoic acid ethyl ester (hydrobromide salt);

(6-aminopyridin-3-ylmethyl)-(benzimidazol-2-ylmethyl)-(5,6,7,8-tetrahydroquinolin-8-yl)-amine (hydrobromide salt);

(2-aminopyridin-3-ylmethyl)-(benzimidazol-2-ylmethyl)-(5,6,7,8-tetrahydro-8-quinolinyl)-amine (hydrobromide salt);

N-(4-{[(H-Benzimidazol-2-ylmethyl)-(5,6,7,8-tetrahydro-quinolin-8-yl)-amino]-methyl}-phenyl)-guanidine (hydrobromide salt);

(4-Amino-benzyl)-(1H-benzoimidazol-2-ylmethyl)-(5,6,7,8-tetrahydro-quinolin-8-yl) -amine (hydrobromide salt);

N'-({[(1H-Benzimidazol-2-ylmethyl)-(5,6,7,8-tetrahydroquinolin-8-yl)-amino]-methyl}-phenyl)-N,N-dimethylformamidine;

4-{[(1H-Benzimidazol-2-ylmethyl)-(5,6,7,8-tetrahydro-quinolin-8-yl)-amino]-methyl}-benzaldehyde oxime;

[4-(1H-benzimidazol-2-ylmethyl)-(5,6,7,8-tetrahydro-quinolin-8-yl)-aminomethyl]-benzamidine (hydrobromide salt);

4-{[(1H-Benzimidazol-2-ylmethyl)-(5,6,7,8-tetrahydro-quinolin-8-yl)-amino]-methyl}-benzyl alcohol;

4-{[(1H-Benzimidazol-2-ylmethyl)-(5,6,7,8-tetrahydro-quinolin-8-yl)-amino]-methyl}-benzaldehyde;

4-{[(1H-Benzimidazol-2-ylmethyl)-(5,6,7,8-tetrahydro-quinolin-8-yl)-amino]-methyl}-benzoic acid methyl ester;

(R,S)-4-{[(1H-Benzimidazol-2-ylmethyl)-(5,6,7,8-tetrahydro-quinolin-8-yl)-amino]-methyl}-N-hydroxybenzamide;

4-{[(H-Benzimidazol-2-ylmethyl)-(5,6,7,8-tetrahydro-quinolin-8-yl)-amino]-methyl}-benzoic acid hydrazide;

4-{[(1H-benzoimidazol-2-ylmethyl)-(5,6,7,8-tetrahydro-quinolin-8-yl)-amino]-methyl}-benzoic acid (hydrobromide salt);

4-{[(1H-Benzimidazol-2-ylmethyl)-(5,6,7,8-tetrahydro-quinolin-8-yl)-amino]-methyl}-benzamide;

(6-Amino-pyridin-2-ylmethyl)-(1H-benzimidazol-2-ylmethyl)-(5,6,7,8-tetrahydro -quinolin-8-yl)-amine (hydrobromide salt);

(2-{[(1H-Benzimidazol-2-ylmethyl)-(5,6,7,8-tetrahydro-quinolin-8-yl)-amino]-methyl}-phenyl)-methanol (free base);

O-(2-{[(1H-Benzimidazol-2-ylmethyl)-(5,6,7,8-tetrahydro-quinolin-8-yl)-amino]-methyl}-benzyl)-hydroxylamine (hydrobromide salt);

(4-Amino-pyridin-3-ylmethyl)-(1H-benzimidazol-2-ylmethyl)-(5,6,7,8-tetrahydro -quinolin-8-yl)-amine (hydrobromide salt);

2-{[(1H-Benzimidazol-2-ylmethyl)-(5,6,7,8-tetrahydro-quinolin-8-yl)-amino]-methyl}-5-cyano-benzoic acid methyl ester;

4-{[(1H-benzimidazol-2-ylmethyl)-(5,6,7,8-tetrahydro-quinolin-8-yl)-amino]-methyl}-3-cyano-benzamide;

[3-(1H-benzimidazol-2-yl)-benzyl]-(1H-benzimidazol-2-ylmethyl)-(5,6,7,8-tetrahydroquinolin-8-yl)-amine (hydrobromide salt);

(1H-Benzimidazol-2-ylmethyl)-(5,6,7,8-tetrahydroquinolin-8-yl)-(imidazol-2-yl) -methylamine (hydrobromide salt);

4-{[(1H-Benzimidazol-2-ylmethyl)-(5,6,7,8-tetrahydro-quinolin-8-yl)-amino]-methyl}-2,6-dichloropyridine (hydrobromide salt);

(1H-benzoimidazol-2-ylmethyl)-benzooxazol-5-ylmethyl-(5,6,7,8-tetrahydro-quinolin-8-yl)-amine;

pyridin-2-ylmethyl-(1H-benzimidazol-2-ylmethyl)-(5,6,7,8-tetrahydroquinolin-8-yl)-amine;

(1H-benzimidazol-2-ylmethyl)-benzoxazol-6-ylmethyl-(5,6,7,8-tetrahydro-quinolin-8-yl)-amine;

(1H-benzimidazol-4-ylmethyl)-(1H-benzimidazol-2-ylmethyl)-(5,6,7,8-tetrahydro--quinolin-8-yl)-amine (hydrobromide salt);

(1H-Benzimidazol-2-ylmethyl)-pyridin-4-ylmethyl-(5,6,7,8-tetrahydro-quinolin-8-yl)-amine;

(1H-Benzimidazol-2-ylmethyl)-(benzo[1,3]dioxol-4-ylmethyl)-(5,6,7,8-tetrahydro -quinolin-8-yl)-amine;

benzo[1,3]dioxol-5-ylmethyl-(1H-benzoimidazol-2-ylmethyl)-(5,6,7,8-tetrahydro -quinolin-8-yl)-amine;

(1H-Benzimidazol-2-ylmethyl)-(2,3-dihydro-benzofuran-7-ylmethyl)-(5,6,7,8-tetrahydro-quinolin-8-yl)-amine (hydrobromide salt);

(1H-Benzimidazol-2-ylmethyl)-pyridin-3-ylmethyl-(5,6,7,8-tetrahydro-quinolin-8-yl) -amine (hydrobromide salt);

(1H-benzoimidazol-5-ylmethyl)-(1H-benzoimidazol-2-ylmethyl)-(5,6,7,8-tetrahydro -quinolin-8-yl)-amine (hydrobromide salt);
Bis-(1H-benzimidazol-2-ylmethyl)-(5,6,7,8-tetrahydro-quinolin-8-yl)-amine (hydrobromide salt);
(1H-Benzimidazol-2-ylmethyl)-(3H-imidazol-4-ylmethyl)-(5,6,7,8-tetrahydro-quinolin -8-yl)-amine (hydrobromide salt);
[4-(1H-benzimidazol-2-yl)-benzyl]-(1H-benzimidazol-2-ylmethyl)-(5,6,7,8-tetrahydroquinolin-8-yl)-amine (hydrobromide salt);
(1H-Benzimidazol-2-ylmethyl)-(4-pyrid-2-yl-benzyl)-(5,6,7,8-tetrahydro-quinolin-8-yl) -amine (hydrobromide salt);
(1H-Benzimidazol-2-ylmethyl)-[4-(oxazol-2-yl)-benzyl]-(5,6,7,8-tetrahydroquinolin-8-yl)-amine (hydrobromide salt);
(1H-Benzimidazol-2-ylmethyl)-(4-imidazol-1-yl-benzyl)-(5,6,7,8-tetrahydro-quinolin-8-yl)-amine (hydrobromide salt);
[4-(thiazol-2-yl)-benzyl]-(1H-benzimidazol-2-ylmethyl)-(5,6,7,8-tetrahydroquinolin-8-yl)-amine (hydrobromide salt);
(1H-Benzimidazol-2-ylmethyl)-[4-(benzothiazol-2-yl)-benzyl]-(5,6,7,8-tetrahydroquinolin-8-yl)-amine (hydrobromide salt);
[4-(benzoxazol-2-yl)-benzyl]-(1H-benzimidazol-2-ylmethyl)-(5,6,7,8-tetrahydroquinolin-8-yl)-amine (hydrobromide salt);
[4-(1H-imidazol-2-yl)-benzyl]-(1H-benzimidazol-2-ylmethyl)-(5,6,7,8-tetrahydroquinolin-8-yl)-amine (hydrobromide salt);
(2'-Aminomethyl-biphenyl-4-ylmethyl)-(1H-benzimidazol-2-ylmethyl)-(5,6,7,8-tetrahydro-quinolin-8-yl)-amine (hydrobromide salt);
(1H-Benzimidazol-2-ylmethyl)-(2'-methoxy-biphenyl-4-ylmethyl)-(5,6,7,8-tetrahydro-quinolin-8-yl)-amine (hydrobromide salt);
(1H-Benzimidazol-2-ylmethyl)-(4-oxazol-5-yl-benzyl)-(5,6,7,8-tetrahydro-quinolin-8-yl)-amine (hydrobromide salt);
(1H-Benzimidazol-2-ylmethyl)-(5,6,7,8-tetrahydro-quinolin-8-yl)-(4-thiophen-2-yl -benzyl)-amine (hydrobromide salt);
(1H-Benzimidazol-2-ylmethyl)-[4-(2-methyl-2H-tetrazol-5-yl)-benzyl]-(5,6,7,8-tetrahydro-quinolin-8-yl)-amine (hydrobromide salt); and
(1H-Benzimidazol-2-ylmethyl)-[4-(5-phenyloxazol-2-yl)-benzyl]-(5,6,7,8-tetrahydroquinolin-8-yl)-amine.

Methods to synthesize the compounds useful in the method of the invention are set forth in the U.S. patents and application incorporated hereinabove by reference.

As provided above, AMD3100 is an antagonist with the CXCR4 chemokine receptor (Gerlach, et al., *J.Biol. Chem.* (2001) 276:14153–14160). This compound interferes with the binding of bone marrow stromal cell derived SDF-1 with CXCR4 on stem cells which leads to the release of hematopoietic stem cells from bone marrow into the circulation (Broxmeyer, et al., *Blood* (2001) 98:811a (Abstract)). In a Phase 1 study at the University of Washington, Seattle, a single dose of 80 μg/kg of AMD-3100 resulted in a WBC count of 17,000/ μl and a peak 6-fold increase in circulating CD34+ progenitor/stem cells at the 6 hour time point (Liles, et al., *Blood* 2001 98:737a (Abstract)). In another recent study mice were injected with rhG-CSF and recombinant rat Stem Cell Factor (rrSCF) in order to mobilize large numbers of bone marrow stem cells into the circulation and then we induced a heart attack. The combination of rrSCF and rhG-CSF provides a peak number of circulating stem cells after 5 daily injections. At 27 days post surgery there was a 68% improvement in survival in the treated group versus the controls. At this time the dead tissue was replaced with regenerating myocardium and all functional parameters tested were improved compared with controls (Orlic, et al., *PNAS* (2001) 98:10344–10349).

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith and Williams Introduction to the Principles of Drug Design*, Smith, H. J.; Wright, $2^{nd}$ ed., London (1988).

The compounds of the invention, as they are polyamines, may be administered prepared in the forms of their acid addition salts or metal complexes thereof. Suitable acid addition salts include salts of inorganic acids that are biocompatible, including HCl, HBr, sulfuric, phosphoric and the like, as well as organic acids such as acetic, propionic, butyric and the like, as well as acids containing more than one carboxyl group, such as oxalic, glutaric, adipic and the like. Typically, at physiological pH, the compounds of the invention will be in the forms of the acid addition salts. Particularly preferred are the hydrochlorides. In addition, when prepared as purified forms, the compounds may also be crystallized as the hydrates.

The compounds of the invention may be administered as sole active ingredients, as mixtures of various compounds of formula (1), and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like.

The compounds of the invention may be formulated for administration to animal subject using commonly understood formulation techniques well known in the art. Formulations which are suitable for particular modes of administration and for compounds of the type represented by those of formula (1) may be found in *Remington's Pharmaceutical Sciences*, latest edition, Mack Publishing Company, Easton, Pa.

Preferably, the compounds are administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds of formula (1) vary according to these considerations, but in general, the compounds are administered in the range of about 0.1 μg/kg–5 mg/kg of body weight; preferably the range is about 1 μg/kg–300 μg/kg of body weight; more preferably about 10 μg/kg–100 μg/kg of body weight. For a typical 70-kg human subject, thus, the dosage range is from about 0.7 μg–350 mg; preferably about 700 μg–21 mg; most preferably about 700 μg–7 mg. Dosages may be higher when the compounds are administered orally or transdermally as compared to, for example, i.v. administration.

The compounds may be administered as a single bolus dose, a dose over time, as in i.v. or transdermal administration, or in multiple dosages.

In addition to direct administration to the subject, the compounds of formula (1) can be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of the compound or compounds of formula (1) alone or in combination with other agents, such as macrophage inflammatory protein is a matter of routine optimization.

Subjects that will respond favorably to the method of the invention include medical and veterinary subjects generally, including human patients. Among other subjects for whom the methods of the invention is useful are cats, dogs, large animals, avians such as chickens, and the like. In general, any subject who would benefit from an elevation of progenitor cells and/or stem cells, or whose progenitor cells and/or stem cells are desirable for stem cell transplantation are appropriate for administration of the invention method.

Typical conditions which may be ameliorated or otherwise benefited by the method of the invention include hematopoietic disorders, such as aplastic anemia, leukemias, drug-induced anemias, and hematopoietic deficits from chemotherapy or radiation therapy. The method of the invention is also useful in enhancing the success of transplantation during and following immunosuppressive treatments as well as in effecting more efficient wound healing and treatment of bacterial inflammation. The method of the present invention is further useful for treating subjects who are immunocompromised or whose immune system is otherwise impaired. Typical conditions which are ameliorated or otherwise benefited by the method of the present invention, include those subjects who are infected with a retrovirus and more specifically who are infected with human immunodeficiency virus (HIV). The method of the invention thus targets a broad spectrum of conditions for which elevation of progenitor cells and/or stem cells in a subject would be beneficial or, where harvesting of progenitor cells and/or stem cell for subsequent stem cell transplantation would be beneficial.

The invention compounds are also administered to regenerate myocardium by mobilizing bone marrow stem cells.

Having now generally described the invention, the same will be more readily understood through reference to the following examples which are provided by way of illustration, and are not intended to be limiting of the present invention, unless specified.

EXAMPLE 1

Elevation of Mouse Progenitor Cell Levels

The effects of subcutaneous (s.c.) administration of 1,1'-[1,4-phenylene-bis(methylene)]-bis-1,4,8,11-tetraazacyclotetradecane (AMD3100) to C3H/H3 J mice on numbers of granulocyte macrophage (CFU-GM), erythroid (BFU-E), and multipotential (CFU-GEMM) progenitor cells per mL of blood were measured. Progenitors were stimulated to form colonies in vitro with the combination of 1 U/ml rhu Epo, 50 ng/ml rhu SLF, 5% Vol/Vol pokeweed mitogen mouse spleen cell conditioned medium (PWMSCM), and 0.1 mM hemin. Plates were scored 7 days after incubation.

The time dependent effects on the number of progenitors mobilized with AMD3100 are for a single s.c. injection of 5 mg/Kg and are shown in Table 1.

TABLE 1

| | Absolute Progenitors Per ML Blood Methylcellulose Culture | | |
|---|---|---|---|
| | CFU-GM | BFU-E | CFU-GEMM |
| Control | 289.8 | 49.4 | 25.8 |
| AMD3100: 15" | 791.6 | 134.5 | 90.4 |
| AMD3100: 30" | 1805.5 | 209.3 | 113.5 |
| AMD3100: 120" | 828.7 | 102.3 | 47.6 |

To measure the dose-dependent effects, AMD3100 was administered at 1, 2.5, 5 and 10 mg/Kg via a single s.c. injection and the number of progenitors per mL of blood was measured at 1 hour post administration, and the results are shown in Table 2.

TABLE 2

| | Absolute Number Progenitors Per ML Blood Methylcellulose Culture | | |
|---|---|---|---|
| | CFU-GM | BFU-E | CFU-GEMM |
| Saline | 188.1 | 16 | 19 |
| AMD3100: 10 mg/kg | 825.6 | 120.5 | 79.8 |
| AMD3100: 5 mg/kg | 608.4 | 92.8 | 69.5 |
| AMD3100: 2.5 mg/kg | 687.6 | 98.9 | 70.6 |
| AMD3100: 1 mg/kg | 424 | 62 | 27.1 |
| Fold Change Compared to Time 0 | | | |
| | Progenitors Methylcellulose Culture | | |
| Time | GM | BFU-E | CFU-GEMM |
| 15" | 2.73 | 2.72 | 3.51 |
| 30" | 6.23 | 4.24 | 4.41 |
| 2' | 2.86 | 2.07 | 1.85 |

Maximum mobilization of mouse progenitors is achieved at a dose of 2.5 to 10 mg/kg AMD3100, approximately 0.5 to 1 hour after injection, as shown in Table 3.

EXAMPLE 2

Mobilization of Mouse Progenitor Cells in Combination with MIP-1α and G-CSF

The progenitor cell mobilization capacity of AMD3100 in combination with mouse (mu) macrophage inflammatory protein (MIP-1α) was tested with or without prior administration of rhu G-CSF. MIP-1α has been previously shown to mobilize progenitor cells in mice and humans (Broxmeyer, H. E., et al., *Blood Cells, Molecules, and Diseases* (1998) 24(2):14–30).

Groups of mice were randomized to receive control diluent (saline) or G-CSF at a dose of 2.5 μg per mouse, twice a day, for two days via s.c. injection. Eleven hours after the final injection of saline or G-CSF, the mice were divided into groups to receive MIP-1α administered I.V. at a total dose of 5 μg, AMD3100 administered s.c. at a dose of 5 mg/Kg, or a combination of both MIP-1α and AMD3100 at the same doses. One hour later, the mice were sacrificed and the number of progenitor cells per mL of blood were measured. These data are summarized in FIG. 1.

AMD3100 acts in an additive to greater than additive manner for mobilization of progenitor cells when used in combination with mouse (mu) macrophage inflammatory protein (MIP)-1α, each given 11 hours after the addition of rhu G-CSF or control diluent (saline) and 1 hour prior to assessing the blood.

EXAMPLE 3

Clinical Elevation of Progenitor Cell Levels

Five healthy human volunteers having initial white blood cell counts of 4,500–7,500 cells/mm$^3$ were used in the study. Each patient was given a single subcutaneous (s.c.) injection of 80 μg/kg AMD3100 (i.e., 1,1'-[1,4-phenylene-bis(methylene)]-bis-1,4,8,11-tetraazacyclotetradecane) in 0.9% saline, from a stock solution of 10 mg/mL AMD3100 in saline, under sterile conditions. Blood samples were obtained via catheter prior to the dose, and at various times up to 24 hours after dosing.

The blood samples were evaluated for total white blood cells, CD34 positive progenitor cells (via FACS analysis) as a percentage of total white blood cells, as well as the absolute numbers per mL and cycling status of granulocyte macrophage (CFU-GM), erythroid (BFU-E), and multipotential (CFU-GEMM) progenitor cells.

As shown in Tables 3 and 4, administration of AMD3100 caused an elevation of the white blood cell count and of CD34 positive progenitor cells in human volunteers which maximized at 6 hours post-administration.

TABLE 3

AMD3100 induced mobilization of white blood cells in individual volunteers (×10$^3$ WBC's).

| | | | | TREATMENT | | | | | |
|---|---|---|---|---|---|---|---|---|---|
| ID | Screen | Base-line | 30 Min | 1 Hr | 2 Hr | 4 Hr | 6 Hr | 9 Hr | Day 2 |
| P1 | 7.4 | 6.41 | 8.02 | 14.8 | 21.4 | 23.2 | 26.2 | 22.3 | 7.07 |
| P2 | 6.04 | 5.45 | 6.53 | 8.93 | 13.5 | 18.00 | 19.2 | 19.6 | 8.03 |
| P3 | 4.38 | 5.8 | 7.14 | 9.28 | ND | 18.10 | 17.9 | 18.4 | 4.98 |

TABLE 3-continued

AMD3100 induced mobilization of white blood cells in individual volunteers (×10$^3$ WBC's).

| | | | | TREATMENT | | | | | |
|---|---|---|---|---|---|---|---|---|---|
| ID | Screen | Base-line | 30 Min | 1 Hr | 2 Hr | 4 Hr | 6 Hr | 9 Hr | Day 2 |
| P4 | 5.08 | 5.31 | 4.37 | 7.38 | 12.4 | 14.6 | 15.8 | 13.9 | 4.98 |
| P5 | 4.53 | 5.02 | 6.08 | 8.43 | ND | 16.90 | 19.3 | 19.00 | 4.57 |

TABLE 4

AMD3100 induced mobilization of CD34 positive cells, expressed as the percentage of the total WBC's in individual volunteers.

| | | TREATMENT | | | |
|---|---|---|---|---|---|
| ID | Baseline | 1 Hr | 3 Hr | 6 Hr | 9 Hr | Day 2 |
| P1 | .07 | .04 | .07 | .11 | .11 | .08 |
| P2 | .08 | .06 | .08 | .13 | .11 | .12 |
| P3 | .07 | .16 | .06 | ND | .11 | .07 |
| P4 | .05 | .07 | .09 | .09 | .1 | .1 |
| P5 | .12 | .12 | .13 | .2 | .2 | .16 |

The blood was also analyzed for AMD3100 mobilized these progenitors.

Absolute numbers of unseparated and low density (Ficohypaque separated) nucleated cells per ml of blood, as well as the absolute numbers per ml and cycling status of granulocyte macrophage (CFU-GM), erythroid (BFU-E), and multipotential (CFU-GEMM) progenitor cells were measured in normal donors injected s.c. with AMD3100. The above parameters were assessed prior to injection and at 1, 3, 6, 9 and 24 hours after injection of AMD3100. All progenitor cell results are based on the scoring of 3 culture plates per assay per point.

For the progenitor cell numbers and cycling status, the numbers of CFU-GM, BFU-E and CFU-GEMM in methylcellulose cultures by stimulation of the cells with 1 Unit (U)/ml recombinant human (rhu) erythropoietin, 100 U/ml rhu granulocyte-macrophage colony stimulating factor (GM-CSF), 100 U/ml rhu interleukin-3 (IL-3) and 50 ng/ml rhu steel factor (SLF=stem cell factor (SCF)). The CFU-GM were also evaluated in agar cultures stimulated with 100 U/ml rhu GM-CSF and 50 ng/ml rhu SLF. For both types of assays, colonies were scored after 14 day incubation in a humidified atmosphere with 5% $CO_2$ and lowered (5%) $O_2$ tension. Cell cycling status of progenitors was measured using a high specific activity tritiated thymidine kill technique as previously described (Broxmeyer, H. E., et al., *Exp. Hematol.* (1989) 17:455–459).

The results are given first, as the mean fold change in absolute numbers of nucleated cells and progenitors at 1, 3, 6, 9 and 24 hours compared to the preinjection (=Time (T) 0) counts for all five donors, as seen in Tables 5–7.

In the tables below,

STD—Standard deviation

STE—Standard error

PBL-US—peripheral blood-unseparated

PBL-LD—peripheral blood-low density (Ficoll Separated)

P—Significance using a 2 tailed t test

TABLE 5

Fold Change Compared to TIME = 0 (Average of 5 donors)

NUCLEATED CELLULARITY

|  | PBL-US | | | | | PBL-LD | | | | |
| --- | --- | --- | --- | --- | --- | --- | --- | --- | --- | --- |
|  | MEAN | STD | STE | % CHG | P | MEAN | STD | STE | % CHG | P |
| T = 0 | 1.00 | 0.00 | 0.00 | 0.0% |  | 1.00 | 0.00 | 0.00 | 0.0% |  |
| T = 1 | 1.69 | 0.00 | 0.00 | 68.6% | 0.017 | 1.86 | 0.00 | 0.00 | 86.2% | 0.000 |
| T = 3 | 2.80 | 0.51 | 0.23 | 180.2% | 0.000 | 2.86 | 0.28 | 0.12 | 185.6% | 0.000 |
| T = 6 | 3.26 | 0.61 | 0.27 | 225.8% | 0.000 | 3.66 | 0.43 | 0.19 | 266.3% | 0.001 |
| T = 9 | 3.09 | 0.69 | 0.31 | 209.4% | 0.000 | 3.64 | 1.18 | 0.53 | 264.3% | 0.001 |
| T = 24 | 1.07 | 0.65 | 0.29 | 7.0% | 0.553 | 1.05 | 1.19 | 0.53 | 4.6% | 0.815 |

TABLE 6

METHYLCELLULOSE CULTURE

|  | CFU-GM | | | | | BFU-E | | | | | CFU-GEMM | | | | |
| --- | --- | --- | --- | --- | --- | --- | --- | --- | --- | --- | --- | --- | --- | --- | --- |
|  | MEAN | STD | STE | % CHG | P | MEAN | STD | STE | % CHG | P | MEAN | STD | STE | % CHG | P |
| T = 0 | 1.00 | 0.00 | 0.00 | 0.0% |  | 1.00 | 0.00 | 0.00 | 0.0% |  | 1.00 | 0.00 | 0.00 | 0.0% |  |
| T = 1 | 4.77 | 0.00 | 0.00 | 376.7% | 0.001 | 1.99 | 0.00 | 0.00 | 98.9% | 0.002 | 2.32 | 0.00 | 0.00 | 131.8% | 0.000 |
| T = 3 | 13.66 | 1.56 | 0.70 | 1266.5% | 0.001 | 3.21 | 0.50 | 0.22 | 221.3% | 0.004 | 4.33 | 0.44 | 0.20 | 332.5% | 0.000 |
| T = 6 | 21.71 | 5.78 | 2.58 | 2070.6% | 0.000 | 6.01 | 1.25 | 0.56 | 500.5% | 0.006 | 10.07 | 0.59 | 0.27 | 907.2% | 0.002 |
| T = 9 | 10.47 | 5.09 | 2.28 | 947.3% | 0.000 | 4.34 | 2.99 | 1.34 | 334.4% | 0.000 | 5.25 | 4.54 | 2.03 | 425.4% | 0.014 |
| T = 24 | 1.56 | 3.01 | 1.34 | 55.5% | 0.005 | 1.26 | 1.02 | 0.45 | 26.3% | 0.194 | 1.53 | 3.04 | 1.36 | 53.2% | 0.199 |

TABLE 7

AGAR CULTURE
CFU-GM

|  | MEAN | STD | STE | % CHG | P |
| --- | --- | --- | --- | --- | --- |
| T = 0 | 1.00 | 0.00 | 0.00 | 0.0% |  |
| T = 1 | 2.81 | 0.00 | 0.00 | 180.8% | 0.001 |
| T = 3 | 8.54 | 0.75 | 0.34 | 754.1% | 0.000 |
| T = 6 | 17.93 | 1.62 | 0.72 | 1692.8% | 0.000 |
| T = 9 | 10.25 | 4.57 | 2.04 | 924.9% | 0.000 |
| T = 24 | 2.08 | 2.06 | 1.03 | 108.3% | 0.073 |

The results are then shown as a fold change from T=0 levels for each individual donor, as shown in Tables 8–10.

TABLE 8

FOLD CHANGE COMPARED TO TIME = 0 for each individual patient [P]

NUCLEATED CELLULARITY

|  | PBL-US | | | | | PBL-LD | | | | |
| --- | --- | --- | --- | --- | --- | --- | --- | --- | --- | --- |
|  | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 |
| T = 1 | 2.54 | 1.38 | 1.38 | 1.36 | 1.76 | 2.07 | 1.99 | 1.48 | 1.66 | 2.10 |
| T = 3 | 3.55 | 2.74 | 2.02 | 2.46 | 3.23 | 2.83 | 3.25 | 2.17 | 2.82 | 3.20 |
| T = 6 | 3.97 | 2.94 | 2.74 | 2.60 | 4.04 | 4.07 | 3.90 | 2.27 | 2.78 | 5.30 |
| T = 9 | 3.27 | 3.30 | 2.69 | 2.24 | 3.96 | 3.65 | 4.43 | 2.47 | 2.48 | 5.17 |
| T = 24 | 1.21 | 1.43 | 0.96 | 0.77 | 0.99 | 1.01 | 1.71 | 0.79 | 0.60 | 1.12 |

TABLE 9

PROGENITORS

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | P1 | P2 | P3 | P4 | P5 | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| T = 1 | 5.09 | 5.33 | 3.70 | 6.87 | 2.84 | 2.58 | 1.48 | 2.30 | 1.46 | 2.13 | 2.07 | 2.26 | 2.22 | 1.96 | 3.07 |
| T = 3 | 7.12 | 17.02 | 15.07 | 20.72 | 8.40 | 5.13 | 1.98 | 2.61 | 2.60 | 3.75 | 4.25 | 3.47 | 4.34 | 5.14 | 4.43 |
| T = 6 | 14.66 | 23.96 | 20.99 | 28.54 | 20.39 | 9.14 | 3.67 | 4.54 | 3.34 | 9.35 | 7.47 | 9.35 | 6.52 | 9.10 | 17.92 |
| T = 9 | 6.26 | 12.51 | 9.42 | 14.08 | 10.09 | 5.43 | 4.61 | 3.71 | 2.93 | 5.05 | 2.64 | 7.09 | 2.47 | 4.52 | 9.55 |
| T = 24 | 1.10 | 1.91 | 1.43 | 1.51 | 1.83 | 1.06 | 1.88 | 1.14 | 0.79 | 1.44 | 1.12 | 2.62 | 0.69 | 0.98 | 2.25 |

TABLE 10

AGAR CULTURE
CFU-GM

| | P1 | P2 | P3 | P4 | P5 |
|---|---|---|---|---|---|
| T = 0 | 1.00 | 1.00 | 1.00 | 1.00 | 1.00 |
| T = 1 | 3.05 | 3.74 | 1.67 | 2.71 | 2.87 |
| T = 3 | 8.88 | 9.49 | 7.47 | 10.46 | 6.40 |
| T = 6 | 17.77 | 24.01 | 14.04 | 13.07 | 20.75 |
| T = 9 | | 10.28 | 7.72 | 10.22 | 12.78 |
| T = 24 | | 3.69 | 1.13 | 1.30 | 2.20 |

The actual nucleated cell and progenitor cell numbers per ml of blood and the cycling status (=% progenitors in DNA synthesis (S) phase of the cell cycle) of progenitors for each of the five donors (#'s P1, P2, P3, P4, and P5) is shown in Tables 11 and 12.

TABLE 11

| | CFU-GM P1 | | BFU-E P1 | | CFU-GEMM P1 | | CFU-GM P2 | | BFU-E P2 | | CFU-GEMM P2 | |
|---|---|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absoulte # of Progenitors per ML | Cycling Status of Progenitors |
| T = 0 | 247 | 6% | 261 | 0% | 127 | 6% | 273 | 0% | 410 | 2% | 120 | 0% |
| T = 1 | 1259 | 1% | 674 | 0% | 264 | 0% | 1455 | 0% | 608 | 3% | 272 | 6% |
| T = 3 | 1760 | 1% | 1340 | 13% | 540 | 7% | 4646 | 2% | 809 | 0% | 418 | 0% |
| T = 6 | 3624 | 0% | 2388 | 0% | 949 | 0% | 6540 | 0% | 1502 | 0% | 1126 | 0% |
| T = 9 | 1547 | 2% | 1418 | 11% | 335 | 0% | 3416 | 0% | 1886 | 0% | 854 | 4% |
| T = 24 | 271 | 0% | 278 | 0% | 142 | 0% | 521 | 3% | 768 | 2% | 316 | 0% |

| | CFU-GM P3 | | BFU-E P3 | | CFU-GEMM P3 | | CFU-GM P4 | | BFU-E P4 | | CFU-GEMM P4 | |
|---|---|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absoulte # of Progenitors per ML | Cycling Status of Progenitors |
| T = 0 | 281 | 0% | 351 | 0% | 140 | 0% | 138 | 0% | 460 | 0% | 101 | 0% |
| T = 1 | 1040 | 0% | 806 | 0% | 312 | 0% | 947 | 0% | 672 | 0% | 199 | 0% |
| T = 3 | 4233 | 1% | 915 | 0% | 610 | 0% | 2857 | 5% | 1195 | 9% | 519 | 0% |
| T = 6 | 5895 | 0% | 1593 | 0% | 916 | 0% | 3936 | 0% | 1533 | 0% | 920 | 8% |
| T = 9 | 2647 | 0% | 1302 | 0% | 347 | 0% | 1942 | 0% | 1348 | 0% | 457 | 0% |
| T = 24 | 402 | 0% | 402 | 0% | 97 | 0% | 208 | 5% | 362 | 3% | 99 | 0% |

| | CFU-GM P5 | | BFU-E P5 | | CFU-GEMM P5 | |
|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors |
| T=0 | 169 | 0% | 343 | 1% | 55 | 0% |
| T=1 | 481 | 0% | 730 | 0% | 169 | 0% |

TABLE 11-continued

| T= 3 | 1423 | 5% | 1288 | 3% | 244 | 0% |
| T= 6 | 3454 | 0% | 3208 | 1% | 987 | 0% |
| T= 9 | 1710 | 0% | 1731 | 0% | 526 | 0% |
| T=24 | 310 | 0% | 495 | 0% | 124 | 0% |

TABLE 12

| | AGAR Culture CFU-GM P1 | | AGAR Culture CFU-GM P2 | | AGAR Culture CFU-GM P3 | | AGAR Culture CFU-GM P4 | | AGAR Culture CFU-GM P5 | |
|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 233 | 6% | 100 | 0% | 140 | 0% | 124 | 0% | 104 | 0% |
| T = 1 | 710 | 0% | 376 | 0% | 234 | 0% | 336 | 0% | 298 | 3% |
| T = 3 | 2070 | 0% | 953 | 1% | 1049 | 0% | 1299 | 0% | 664 | 0% |
| T = 6 | 4142 | 0% | 2409 | 3% | 1972 | 3% | 1623 | 0% | 2153 | 1% |
| T = 9 | | | 1032 | 0% | 1085 | 0% | 1268 | 0% | 1326 | 0% |
| T = 24 | | | 371 | 0% | 159 | 0% | 162 | 0% | 229 | 0% |

The results for all five donors were very consistent with maximal fold increases in circulating levels of progenitor cells seen 6 hours after injection of AMD3100 into the human donor subjects. Progenitors were in a slow or non-cycling state prior to and 1, 3, 6, 9 and 24 hours after injection of AMD3100.

EXAMPLE 4

Mobilized Bone Marrow Stem Cells for Myocardial Repair

Adult rats are anesthetized and a thoracotomy is performed. The descending branch of the left coronary artery is ligated and not reperfused. Within 4 to 6 hours after ligation the animals are injected with limit dilution AMD-3100 or AMD-3100 plus rhG-CSF. Control rats are not treated with the reagents. The animals are monitored at one-week intervals by echocardiography and MRI. The experiment is terminated at 2, 6 to 12 weeks post-surgery. On the day of sacrifice, the hemodynamic functions are analyzed for left ventricle-end diastolic pressure, left ventricle-developed pressure and the rate of rise and fall of left ventricle pressure. The heart is then arrested in diastole and perfuised via the abdominal aorta to flush residual blood from the vascular network of the myocardium. This is followed by perfusion of the heart with 10% formalin. Several slices are made through the fixed heart and these are embedded in paraffin and sections. The sections are stained and analyzed by light microscopy to determine the size of the infarct in the treated and control animals. Tissue sections from hearts taken at 2 weeks after surgery are stained with antibodies specific for immature, developing myocyte and blood vessel proteins and analyzed by confocal microscopy. The immunohistochemical analysis involves the identification of transcription factors and surface markers expressed in early stages of myocyte development. The results of this experiment will show that when the reagent AMD-3100 is administered within hours after induction of cardiac ischemia, together with or without rhG-CSF, this reagent mobilizes bone marrow stem cells rapidly, and will result in a block to cardiac remodeling and scar formation and will lead to regeneration of the dead myocardium.

The invention claimed is:

1. A method to obtain progenitor and/or stem cells, from a subject, which method comprises
   (a) administering to said subject a compound of the formula Z-linker-Z'     (1)

or pharmaceutically acceptable salt or prodrug form thereof
   wherein Z is of the formula

wherein A comprises a monocyclic or bicyclic fused ring system containing at least one N and B is H or an organic moiety of 1–20 atoms,
   Z' is of the formula —Ar(Y)$_j$;

wherein Ar is an aromatic or heteroaromatic moiety, and each Y is independently a non-interfering substituent and j is 0–3; and
   "linker" represents a bond, alkylene (1–6C) or may comprise aryl, fused aryl, oxygen atoms contained in an alkylene chain, or may contain keto groups or nitrogen or sulfur atoms;
   in an amount effective to mobilize said progenitor and/or stem cell population in said subject; followed by
   (b) harvesting said progenitor and/or stem cells.

2. The method of claim 1 wherein the compound of formula (1) is of the formula:

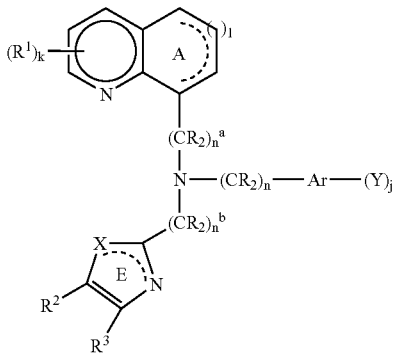

(2)

and salts and prodrug forms thereof
wherein:
Ring A optionally comprises a heteroatom selected from N, O and S;
the dotted lines represent optional unsaturation;
R1, R2 and R3 are non-interfering substituents;
k is 0–4;
l is 0, 1, or 2;
X is unsubstituted or substituted C or N; or is O or S;
Ar is the residue of an aromatic or heteroaromatic moiety;
each n is independently 0–2;
each R is independently H or alkyl (1–6C);
j is 0–3; and
each Y is independently halo, OH, SH, SO, $SO_2$, or an organic moiety of 1–20C atoms that does not contain N wherein two such Y may be connected to form a fused ring with Ar, or is selected from the group consisting of
—$(CR_2)_m CN$,
—$(CR_2)_m NR^5{}_2$,
—$(CR_2)_m NR(CR_2)_m NRR^4$,
—$(CR_2)_m NR(CR_2)_m NR(CR_2)m NR^5{}_2$,
—$(CR_2)_m CO(CR_2)_m NR^5{}_2$,
—$(CR_2)_m CO(CR_2)_m NR(CR_2)_m NRR^4$,
—$(CR_2)_m CO(CR_2)_m NR(CR_2)_m NR(CR_2)_m NR^5{}_2$,
—$(CR_2)_m NRCO(CR_2)_m NRR^4$,
—$(CR_2)_m NRCO(CR_2)_m NR(CR_2)_m NR^5{}_2$,
—$(CR_2)_m NRCO(CR_2)_m NR(CR_2)_m NR(CR_2)_m NR(CR_2)_m NR^5{}_2$,
—CH=N—Z",
—$(CR_2)_m Z"$,
—NR $(CR_2)_m Z"$,
—$(CR_2)_m NROH$,
$(CR_2)_m CONROH$, and
$(CR_2)_m CR$=NOH,
wherein Z" is an optionally substituted aromatic or heteroaromatic moiety containing 5–12 ring members; and
wherein R is as defined above, each m is independently 0–4, and $R_4$ and each $R^5$ is independently H, alkyl (1–6C), alkenyl (1–6C), alkynyl (1–6C), or acyl (1–6C), each optionally substituted by one or more nonaromatic, nonheterocyclic substituent(s), and wherein two $R^5$ may be connected to form a cyclic amine, optionally containing one or more additional heteroatoms selected from N, O, and S.

3. The method of claim 2 wherein ring E is coupled to the remainder of the molecule at position 2.

4. The method of claim 3 wherein $R^2$ and $R^3$ taken together form a benzo substituent.

5. The method of claim 4 wherein X is N and ring E comprises a pi bond coupled to one N.

6. The method of claim 2 wherein ring A is saturated and l is 1.

7. The method of claim 6 wherein k is 0–1.

8. The method of claim 7 wherein the ring system which includes A is tetrahydroquinoline or a substituted form thereof.

9. The method of claim 2 wherein one of $(CR_2)^a{}_n$ and $(CR_2)^b{}_n$ is $CH_2$ and the other is a bond.

10. The method of claim 9 wherein $(CR_2)^a{}_n$ is a bond and $(CR_2)^b{}_n$ is $CH_2$.

11. The method of claim 2 wherein at least one Y is —$CH_2NH_2$.

12. The method of claim 2 wherein Ar is the residue of benzene, benzimazole, benzothiazole, imidazole, oxazole, benztriazole, thiazole, pyridine, or pyrimidine.

13. The method of claim 1 wherein formula (1) is in the form of its acid addition salt.

14. The method of claim 13 wherein the acid addition salt is a hydrochloride.

15. The method of claim 1 wherein the subject is a healthy stem cell donor.

16. The method of claim 1 wherein the compound is administered to said subject by an intravenous or subcutaneous route.

17. The method of claim 1 wherein the compound of formula (1) is administered to said subject in a dosage range of about 0.1 µg/kg–5 mg/kg of body weight.

18. The method of claim 1 which further comprises administering macrophage inflammatory protein to said subject.

19. The method of claim 1 which further includes the step of administering G-CSF to said subject prior to performing the method.

20. The method of claim 1 wherein the subject is human.

21. The method of claim 1 wherein the harvesting is by apheresis.

* * * * *